US009755152B2

United States Patent
Yokoyama et al.

(10) Patent No.: US 9,755,152 B2
(45) Date of Patent: *Sep. 5, 2017

(54) COMPOUND HAVING SUBSTITUTED ANTHRACENE RING STRUCTURE AND PYRIDOINDOLE RING STRUCTURE, AND ORGANIC ELECTROLUMINESCENT DEVICE

(71) Applicant: Hodogaya Chemical Co., Ltd., Tokyo (JP)

(72) Inventors: Norimasa Yokoyama, Tokyo (JP); Shuichi Hayashi, Tsukuba (JP); Naoaki Kabasawa, Tokyo (JP); Daizou Kanda, Tokyo (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 185 days.

This patent is subject to a terminal disclaimer.

(21) Appl. No.: 14/552,576

(22) Filed: Nov. 25, 2014

(65) Prior Publication Data

US 2015/0155496 A1 Jun. 4, 2015

Related U.S. Application Data

(63) Continuation of application No. 13/388,123, filed as application No. PCT/JP2010/004784 on Jul. 28, 2010, now Pat. No. 8,927,119.

(30) Foreign Application Priority Data

Aug. 5, 2009 (JP) .................................. 2009-182019

(51) Int. Cl.
*H01L 51/50* (2006.01)
*H01L 51/00* (2006.01)
(Continued)

(52) U.S. Cl.
CPC ........ *H01L 51/0052* (2013.01); *C07D 471/04* (2013.01); *C07D 519/00* (2013.01);
(Continued)

(58) Field of Classification Search
None
See application file for complete search history.

(56) References Cited

U.S. PATENT DOCUMENTS

2006/0251918 A1  11/2006 Iwakuma et al.
2007/0205412 A1  9/2007 Bae et al.
(Continued)

FOREIGN PATENT DOCUMENTS

CN  101395105 A  3/2009
KR  10-2009-0098646 A  9/2009
(Continued)

OTHER PUBLICATIONS

International Search Report dated Aug. 24, 2010, issued for PCT/JP2010/004784.
(Continued)

*Primary Examiner* — Gregory Clark
(74) *Attorney, Agent, or Firm* — Locke Lord LLP

(57) ABSTRACT

There is provided an organic compound having excellent characteristics, including excellent electron-injecting/transporting performance, hole blocking ability, and high stability in the thin-film state, for use as material of an organic electroluminescent device having high efficiency and high durability. There is also provided a high-efficient and high-durable organic electroluminescent device using the compound. The compound is represented by general formula (1) having a substituted anthracene ring structure and a pyridoindole ring structure. The organic electroluminescent device includes a pair of electrodes, and one or more organic
(Continued)

← 9 CATHODE
← 8 ELECTRON INJECTION LAYER
← 7 ELECTRON TRANSPORT LAYER
← 6 HOLE BLOCKING LAYER
← 5 LIGHT EMITTING LAYER
← 4 HOLE TRANSPORT LAYER
← 3 HOLE INJECTION LAYER
← 2 TRANSPARENT ANODE
← 1 GLASS SUBSTRATE layers sandwiched between the pair of electrodes, and the compound is used as a constituent material of at least one organic layer.

[Chemical Formula 1]

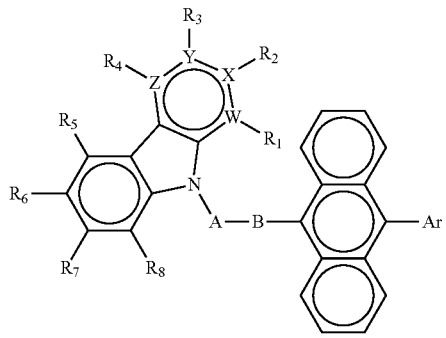

12 Claims, 6 Drawing Sheets

(51) Int. Cl.
C07D 471/04 (2006.01)
C07D 519/00 (2006.01)

(52) U.S. Cl.
CPC ...... H01L 51/0058 (2013.01); H01L 51/0067 (2013.01); H01L 51/0072 (2013.01); *H01L 51/508* (2013.01); *H01L 51/5012* (2013.01); *H01L 51/5048* (2013.01); *H01L 51/5092* (2013.01); *H01L 51/5096* (2013.01); *Y10S 428/917* (2013.01)

(56) References Cited

U.S. PATENT DOCUMENTS

| 2009/0230857 A1* | 9/2009 | Choi ............... C07D 471/04 313/504 |
| 2010/0123388 A1 | 5/2010 | Yokoyama et al. |
| 2010/0230660 A1* | 9/2010 | Yokoyama ........ C07D 471/04 257/40 |
| 2010/0308322 A1 | 12/2010 | Yokoyama et al. |
| 2011/0006291 A1 | 1/2011 | Yokoyama et al. |
| 2011/0073852 A1 | 3/2011 | Yokoyama et al. |
| 2011/0175079 A1 | 7/2011 | Yokoyama et al. |

FOREIGN PATENT DOCUMENTS

| TW | 200815403 A | 4/2008 |
| TW | 200902678 A | 1/2009 |
| WO | WO-2004/053019 A1 | 6/2004 |
| WO | WO-2007/102683 A1 | 9/2007 |
| WO | WO-2008/020611 A1 | 2/2008 |
| WO | WO-2008/114690 A1 | 9/2008 |
| WO | WO-2008/127057 A1 | 10/2008 |
| WO | WO-2009/096549 A1 | 8/2009 |
| WO | WO-2009/102016 A1 | 8/2009 |
| WO | WO-2009/139475 A1 | 11/2009 |
| WO | WO-2010/035723 A1 | 4/2010 |

OTHER PUBLICATIONS

Supplementary European Search Report Dated Oct. 8, 2012, issued for the corresponding European Patent Application No. 10806202.7.
Notification of Office Action issued in corresponding Chinese Patent Application No. CN 201080034572.1, dated Apr. 21, 2014.
Office Action issued in corresponding Taiwanese Patent Application No. TW 099125932 dated Jul. 9, 2014.
Office Action dated Jan. 13, 2017, issued for the corresponding Korean application and Japanese translation thereof.

* cited by examiner

[FIG.1]
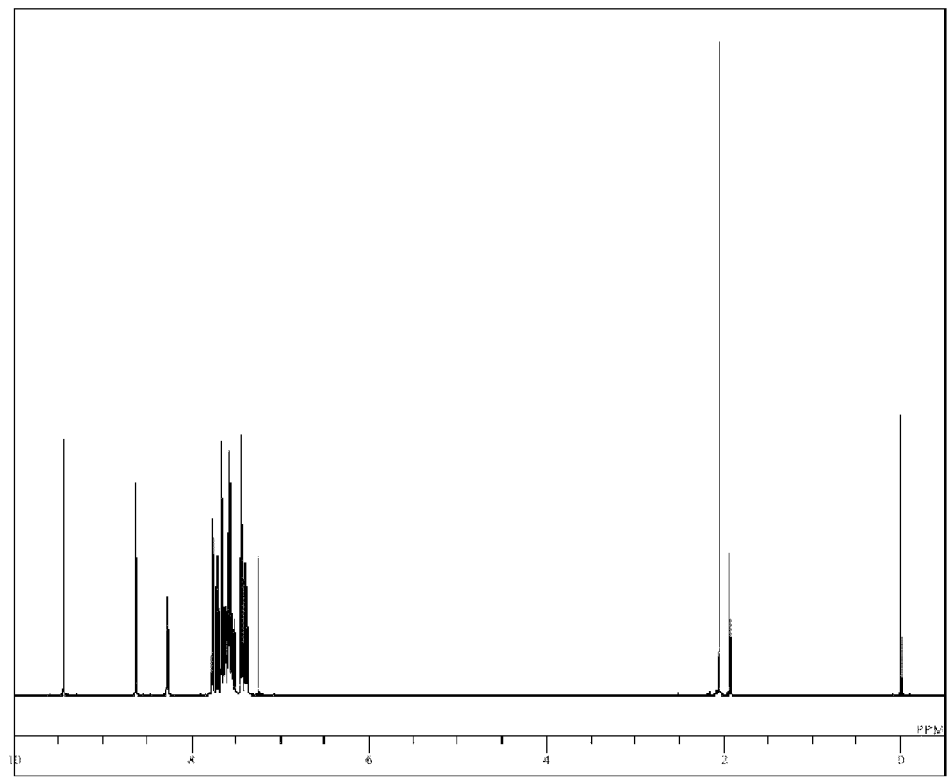
[FIG.2]
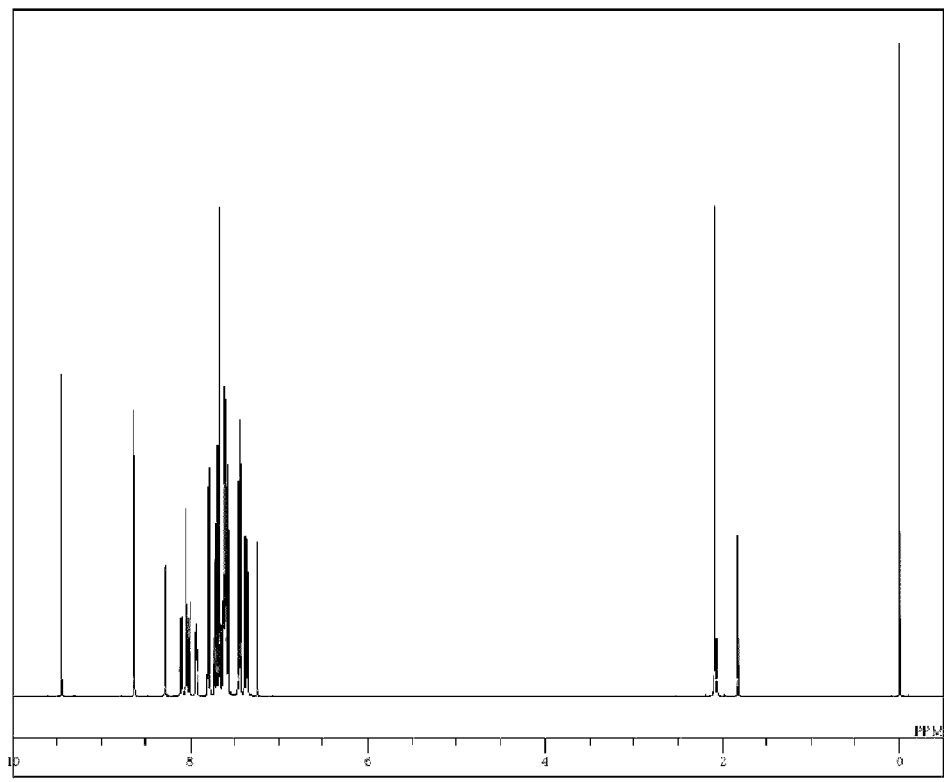

[FIG.3]
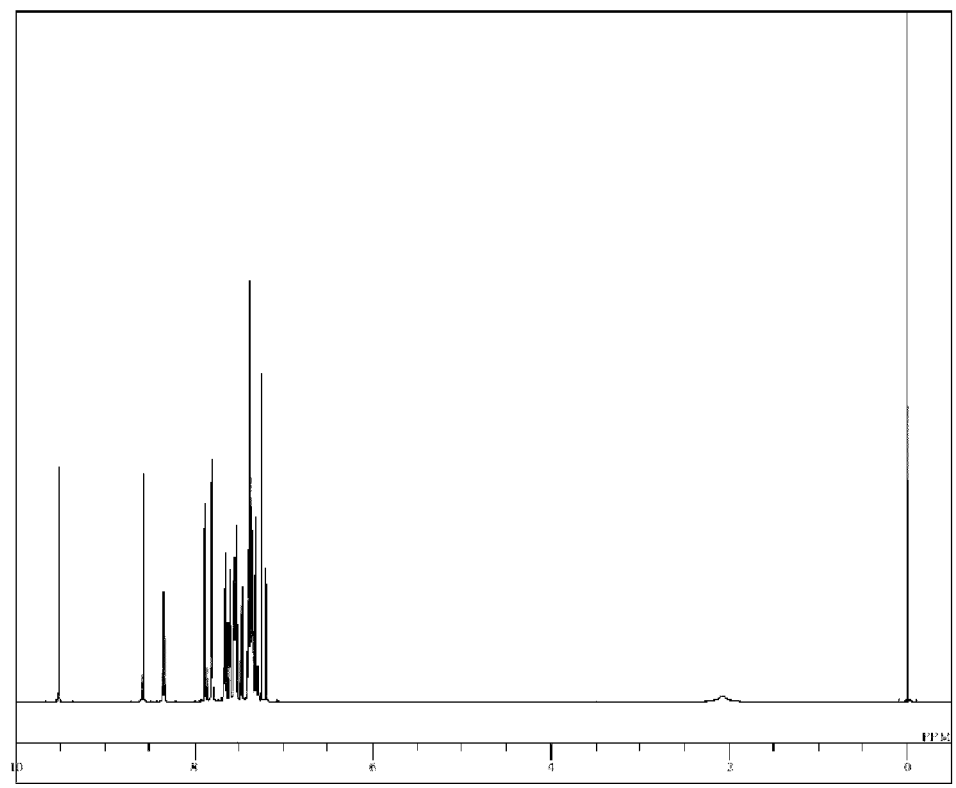
[FIG.4]
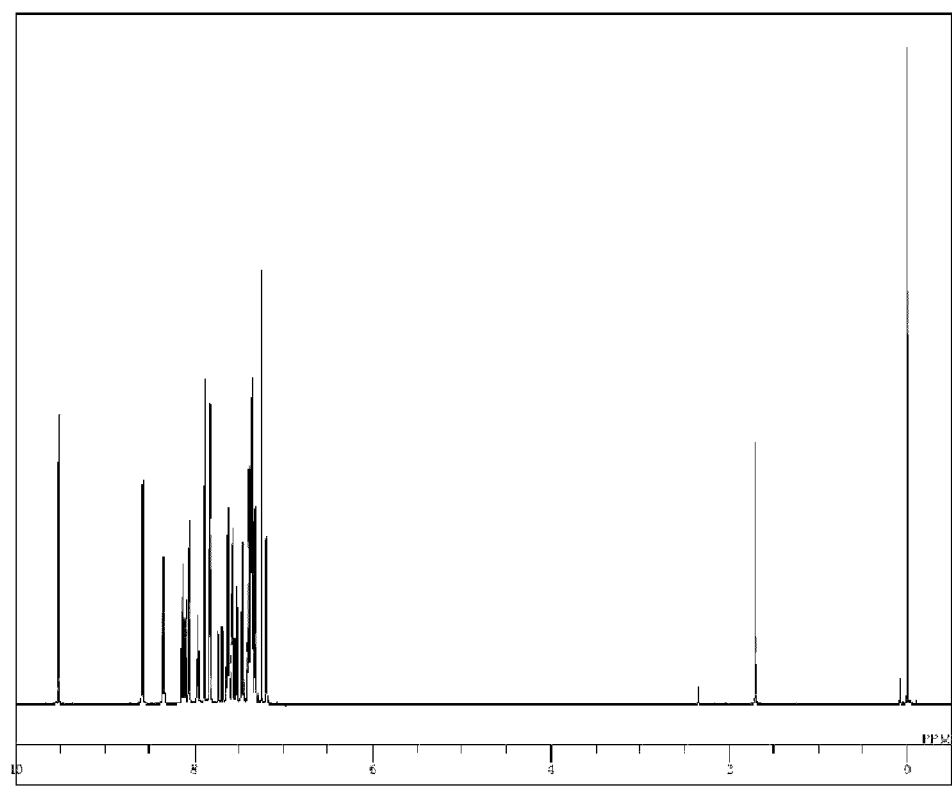

[FIG.5]
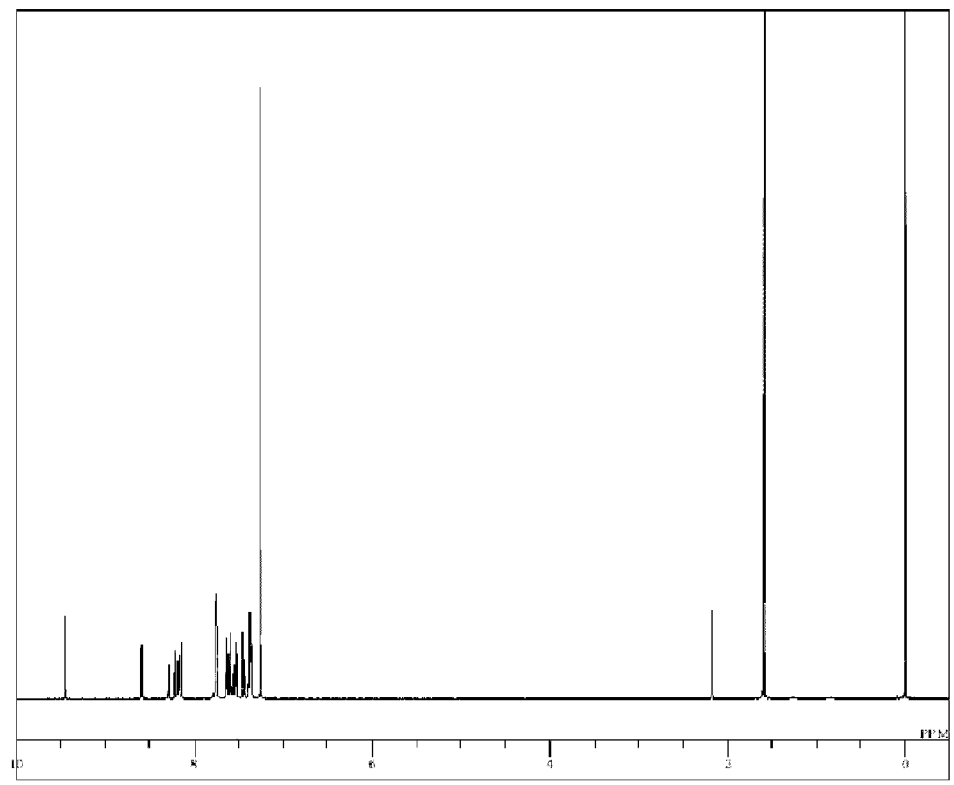
[FIG.6]
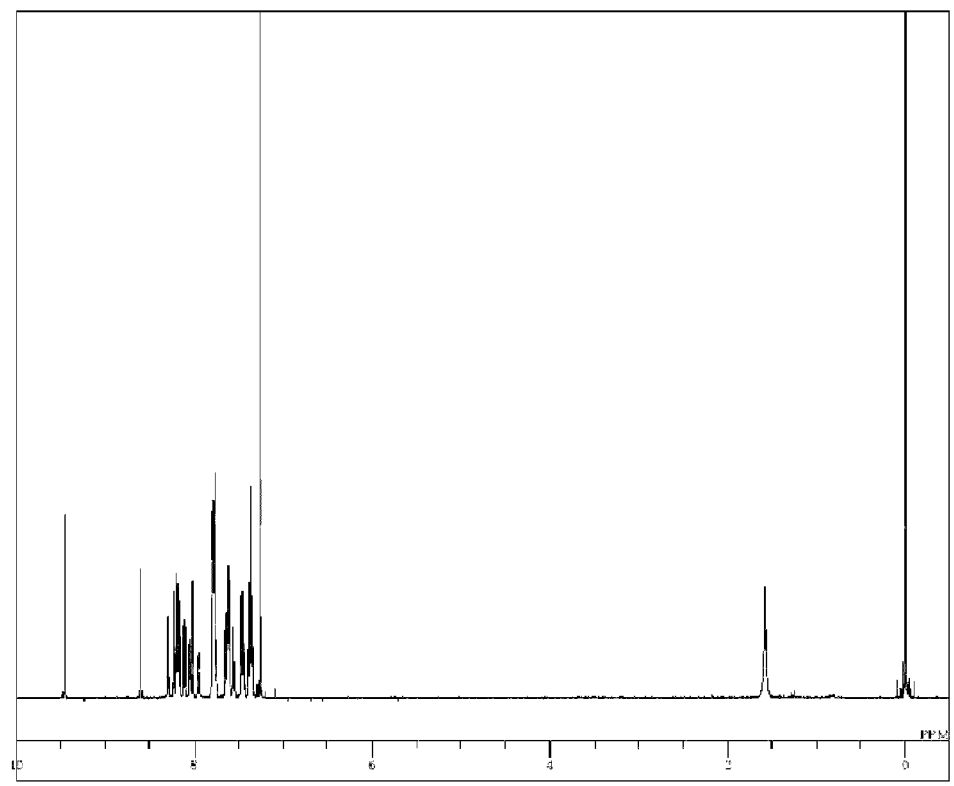

[FIG.7]
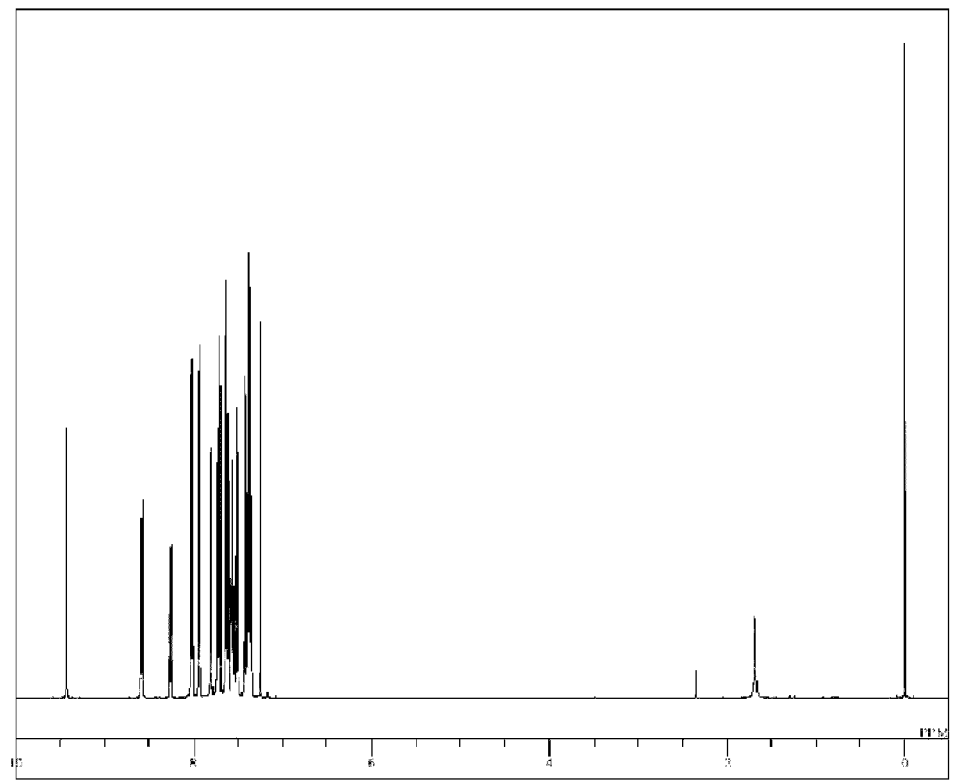
[FIG.8]
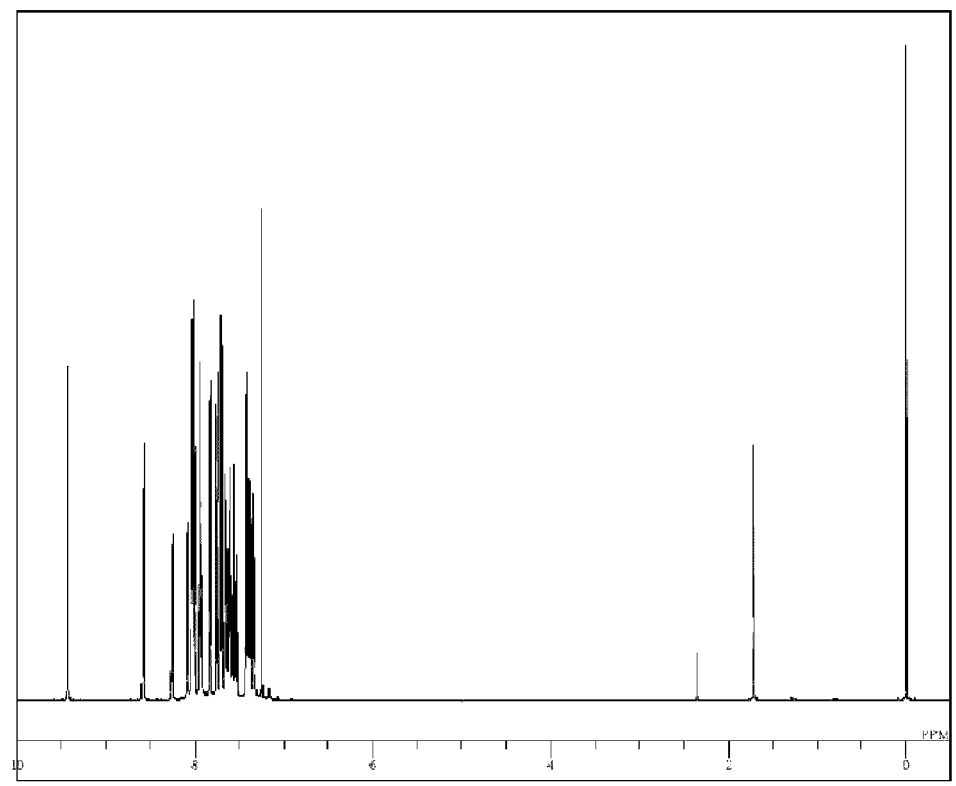

[FIG.9]
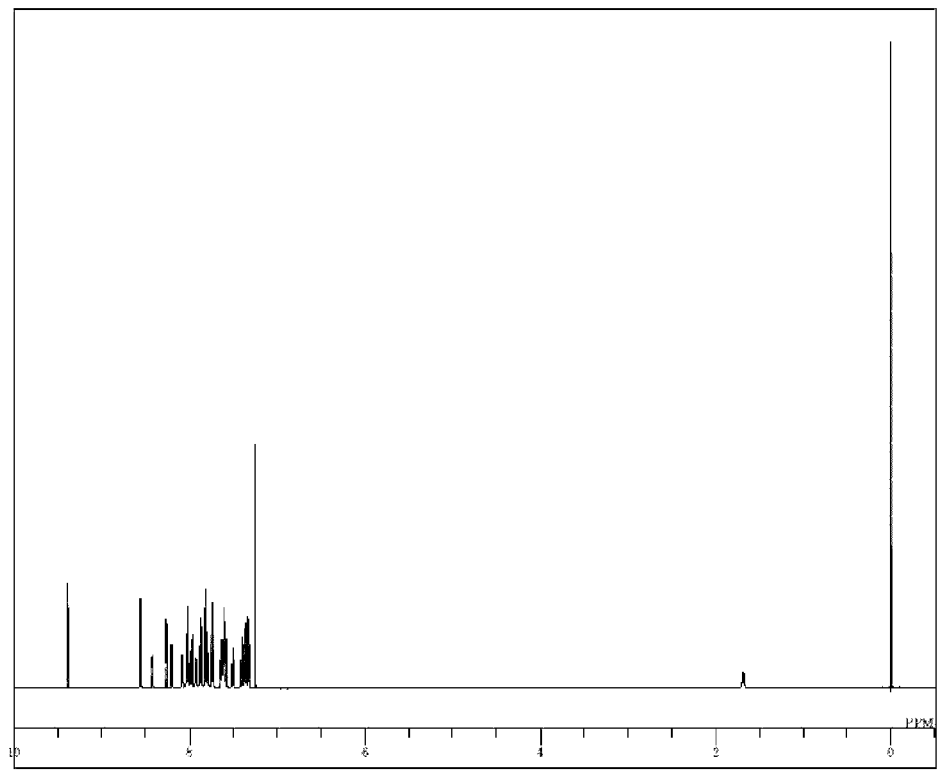
[FIG.10]
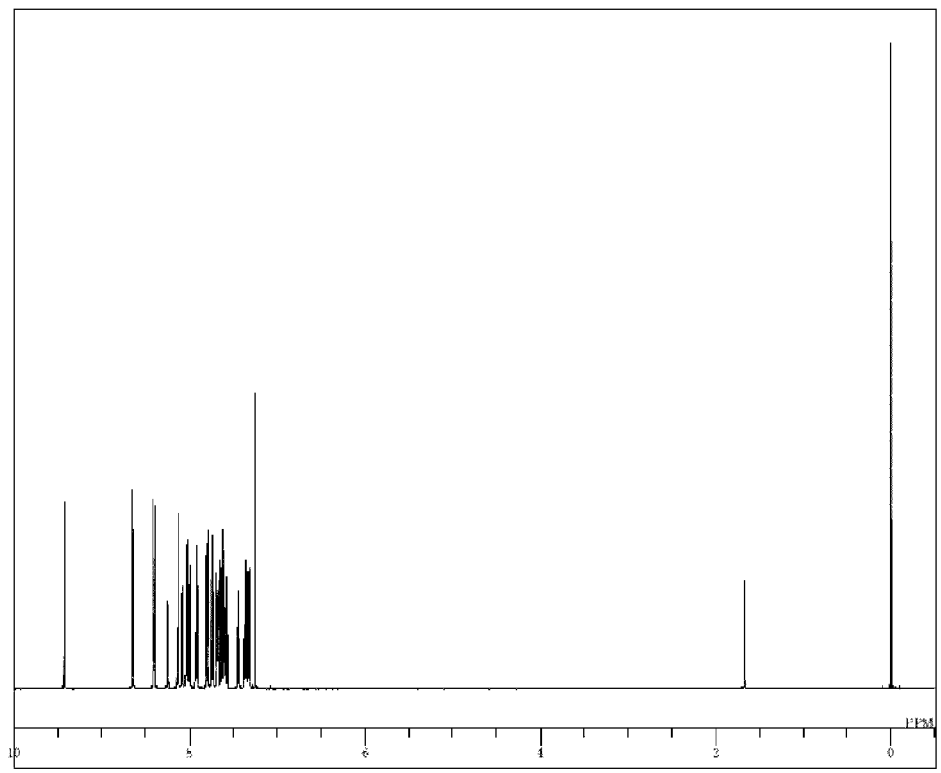

[FIG.11]
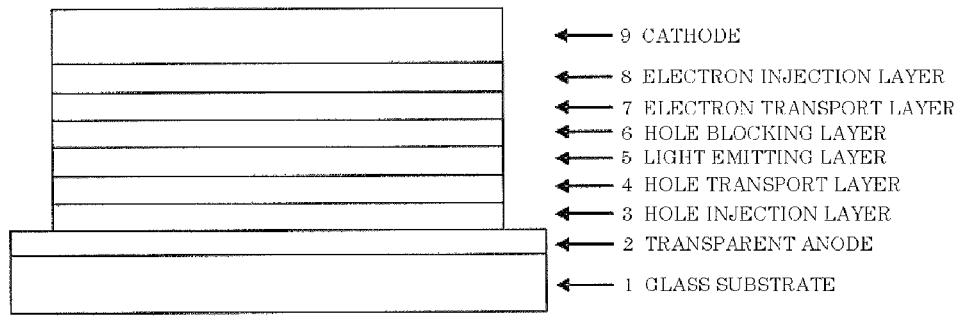
[FIG.12]
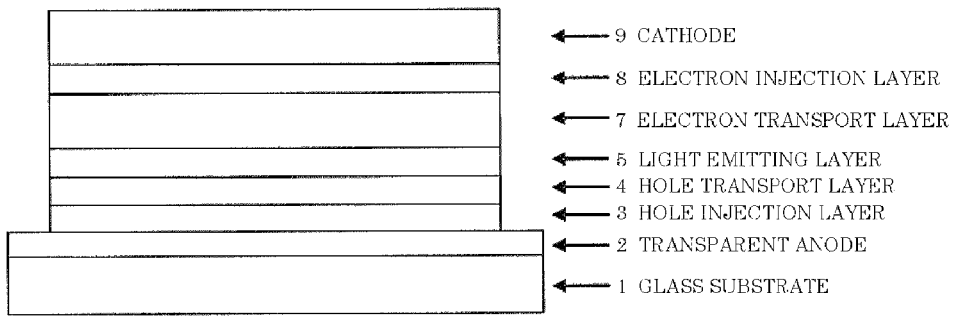
[FIG.13]
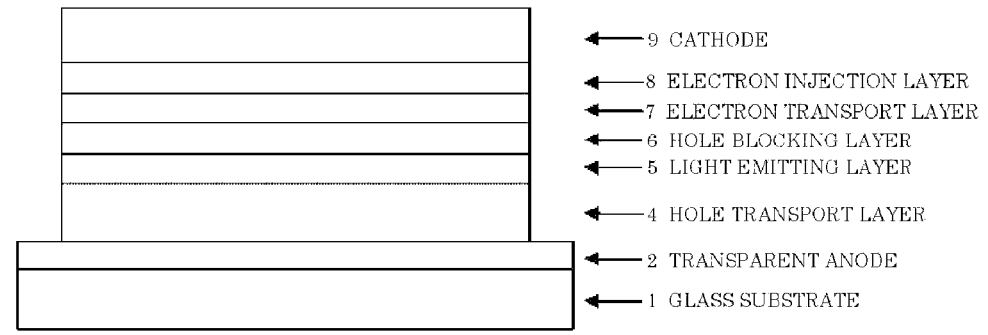
[FIG.14]
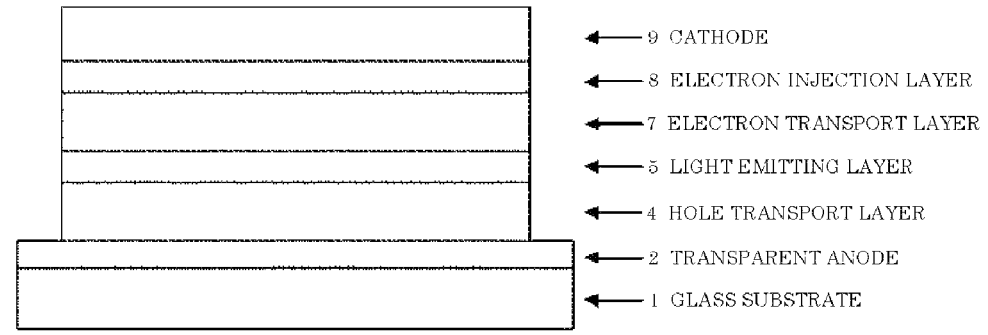

COMPOUND HAVING SUBSTITUTED ANTHRACENE RING STRUCTURE AND PYRIDOINDOLE RING STRUCTURE, AND ORGANIC ELECTROLUMINESCENT DEVICE

TECHNICAL FIELD

The present invention relates to compounds suited for an organic electroluminescent device, a preferred self light-emitting device for various display devices, and to the device. Specifically, the invention relates to compounds having a substituted anthracene ring structure and a pyridoindole ring structure, and organic electroluminescent devices using such compounds.

BACKGROUND ART

The organic electroluminescent device is a self-emitting device, and has been actively studied for their brighter, superior viewability and the ability to display clearer images compared with the liquid crystal device.

In 1987, C. W. Tang and colleagues at Eastman Kodak developed a laminated structure device using materials assigned with different roles, realizing practical applications of an organic electroluminescent device with organic materials. These researchers laminated an electron-transporting phosphor and a hole-transporting organic material, and injected the both charges into the phosphor layer to cause emission in order to obtain a high luminance of 1,000 cd/m$^2$ or more at a voltage of 10 V or less (see, for example, Patent Documents 1 and 2).

To date, various improvements have been made for practical applications of the organic electroluminescent device. In order to realize high efficiency and durability, various roles are further subdivided to provide an electroluminescence device that includes an anode, a hole injection layer, a hole transport layer, a light emitting layer, an electron transport layer, an electron injection layer, and a cathode successively formed on a substrate (see, for example, Non-Patent Document 1).

Further, there have been attempts to use triplet excitons for further improvements of luminous efficiency, and use of phosphorescent materials have been investigated (see, for example, Non-Patent Document 2).

The light emitting layer can be also fabricated by doping a charge-transporting compound, generally called a host material, with a phosphor or a phosphorescent material. As described in the foregoing lecture preprints, selection of organic materials in an organic electroluminescent device greatly influences various device characteristics, including efficiency and durability.

In an organic electroluminescent device, the charges injected from the both electrodes recombine at the light emitting layer to cause emission. However, because the hole mobility is faster than the electron mobility, some of the holes pass through the light emitting layer. This is problematic as it lowers efficiency. Accordingly, there is a need for an electron transport material with fast electron mobility.

Tris(8-hydroxyquinoline)aluminum (hereinafter, "Alq$_3$"), a representative light-emitting material, is generally used also as an electron transport material. However, with a work function of 5.8 eV, the material cannot be said as having hole blocking performance.

Insertion of a hole blocking layer is one method of preventing the passage of some of the holes through the light emitting layer and improving the probability of charge recombination at the light emitting layer. Examples of the hole blocking materials proposed so far include triazole derivatives (for example, see Patent Document 3), bathocuproin (hereinafter, "BCP"), and a mixed ligand complex of aluminum (BAlq) (see, for example, Non-Patent Document 2).

On the other hand, 3-(4-biphenylyl)-4-phenyl-5-(4-t-butylphenyl)-1,2,4-triazole (hereinafter, "TAZ") is proposed as an electron transport material having excellent hole blocking performance (see, for example, Patent Document 3).

TAZ has a large work function of 6.6 eV and a high hole blocking ability, and is thus used as an electron-transporting hole blocking layer laminated on the cathode side of a fluorescent layer or a phosphorescent layer produced by methods such as vacuum vapor deposition and coating. TAZ thus contributes to improving the efficiency of an organic electroluminescent device (see, for example, Non-Patent Document 3).

One big problem of TAZ, however, is the poor electron transportability, and the material is required to be combined with an electron transport material having higher electron transportability for the production of an organic electroluminescent device (see, for example, Non-Patent Document 4).

BCP has a large work function of 6.7 eV and a high hole blocking ability. However, the low glass transition point (Tg) of 83° C. makes the thin film stability poor, and the material cannot be said as being sufficiently functional as a hole blocking layer.

Either of the materials lacks film stability, or does not sufficiently serve to block the holes. In order to improve the characteristics of an organic electroluminescent device, there is a need for an organic compound that exhibits excellent electron-injecting/transporting performance with high hole blocking ability, and has high stability in the thin-film state.

CITATION LIST

Patent Documents

Patent Document 1: JP-A-8-48656
Patent Document 2: Japanese Patent No. 3194657
Patent Document 3: Japanese Patent No. 2734341

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: The 50th Applied Physics-Associated Joint Lecture Presentation, 28p-A-6, Lecture Preprints, p. 1413 (2003)
Non-Patent Document 4: The Japan Society of Applied Physics, Molecular Electronics and Bioelectronics Journal, Vol. 11, No. 1, pp. 13 to 19 (2000)
Non-Patent Document 5: J. Chem. Soc., Perkin Trans. 1, 1505 (1999)
Non-Patent Document 6: J. Org. Chem., 60, 7508 (1995)
Non-Patent Document 7: Synth. Commun., 11, 513 (1981)

SUMMARY OF THE INVENTION

Problems that the Invention is to Solve

It is an object of the present invention to provide an organic compound of excellent characteristics that exhibits excellent electron-injecting/transporting performance with hole blocking ability, and has high stability in the thin-film state, the organic compound being provided as material for an organic electroluminescent device having high efficiency and high durability. The invention also provides a high-efficiency, high-durable organic electroluminescent device using the compound.

Some of the physical properties of the organic compound to be provided by the present invention include (1) good electron injection characteristics, (2) fast electron mobility, (3) excellent hole blocking ability, (4) stability in the thin-film state, and (5) excellent heat resistance. Some of the physical properties of the organic electroluminescent device to be provided by the present invention include (1) high luminous efficiency and high power efficiency, (2) low turn on voltage, and (3) low actual driving voltage.

Means for Solving the Problems

In order to achieve the foregoing objects, the present inventors focused on the high electron transporting ability and the excellent heat resistance of a pyridoindole ring structure, and produced various test organic electroluminescent devices using compounds designed and chemically synthesized to have a substituted anthracene ring structure and a pyridoindole ring structure. The present invention was completed after thorough evaluations of the device characteristics.

Specifically, the present invention is a compound having a substituted anthracene ring structure and a pyridoindole ring structure, represented by the general formula (1) below. Further, the present invention is an organic electroluminescent device that includes a pair of electrodes and one or more organic layers sandwiched between the electrodes, wherein the compound is used as a constituent material of at least one organic layer.

[Chemical Formula 1]

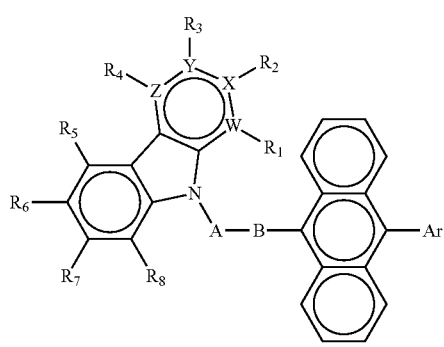

(1)

(In the formula, Ar represents substituted or unsubstituted aromatic hydrocarbon, or substituted or unsubstituted condensed polycyclic aromatic, A represents a divalent group of substituted or unsubstituted aromatic hydrocarbon, a divalent group of a substituted or unsubstituted aromatic heterocyclic ring, or a divalent group of substituted or unsubstituted condensed polycyclic aromatic, B represents a single bond, a divalent group of substituted or unsubstituted aromatic hydrocarbon, a divalent group of a substituted or unsubstituted aromatic heterocyclic ring, or a divalent group of substituted or unsubstituted condensed polycyclic aromatic, R1 to R8 may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom. Here, only one of W, X, Y, and Z is a nitrogen atom, and, in this case, the nitrogen atom does not have the substituents R1 to R4.)

Specific examples of "aromatic hydrocarbon" or "condensed polycyclic aromatic" in the "substituted or unsubstituted aromatic hydrocarbon" or "substituted or unsubstituted condensed polycyclic aromatic" represented by Ar in general formula (1) include phenyl, biphenylyl, terphenylyl, naphthyl, anthryl, phenanthryl, fluorenyl, indenyl, and pyrenyl.

Specific examples of "substituent" in the "substituted aromatic hydrocarbon" or "substituted condensed polycyclic aromatic" represented by Ar in general formula (1) include a deuterium atom, a fluorine atom, a chlorine atom, cyano, hydroxyl, nitro, linear or branched alkyl of 1 to 6 carbon atoms, cyclopentyl, cyclohexyl, linear or branched alkoxy of 1 to 6 carbon atoms, dialkylamino substituted with linear or branched alkyl of 1 to 6 carbon atoms, phenyl, naphthyl, anthryl, fluorenyl, styryl, pyridyl, pyridoindolyl, quinolyl, and benzothiazolyl. These substituents may be further substituted.

Specific examples of "aromatic hydrocarbon", "aromatic heterocyclic group", or "condensed polycyclic aromatic" in the "substituted or unsubstituted aromatic hydrocarbon", "substituted or unsubstituted aromatic heterocyclic group", or "substituted or unsubstituted condensed polycyclic aromatic" represented by R1 to R8 in general formula (1) include phenyl, biphenylyl, terphenylyl, tetrakisphenyl, styryl, naphthyl, anthryl, acenaphthenyl, fluorenyl, phenanthryl, indenyl, pyrenyl, pyridyl, triazyl, pyrimidyl, furanyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, acridinyl, and pyridoindolyl.

Specific examples of "substituent" in the "substituted aromatic hydrocarbon", "substituted aromatic heterocyclic group", or "substituted condensed polycyclic aromatic" represented by R1 to R8 in general formula (1) include a deuterium atom, a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, pyrenyl, and pyridoindolyl. These substituents may be further substituted.

Specific examples of "linear or branched alkyl of 1 to 6 carbon atoms" in the "linear or branched alkyl of 1 to 6 carbon atoms that may have a substituent" represented by R1 to R8 in general formula (1) include methyl, ethyl, n-propyl, i-propyl, n-butyl, i-butyl, t-butyl, n-pentyl, i-pentyl, t-pentyl, n-hexyl, i-hexyl, and t-hexyl.

Specific examples of "substituent" in the "linear or branched alkyl of 1 to 6 carbon atoms having a substituent" represented by R1 to R8 in general formula (1) include a deuterium atom, a fluorine atom, a chlorine atom, phenyl, biphenylyl, terphenylyl, tetrakisphenyl, naphthyl, fluorenyl, phenanthryl, indenyl, pyrenyl, and pyridoindolyl. These substituents may be further substituted.

Specific examples of "divalent group of aromatic hydrocarbon", "divalent group of an aromatic heterocyclic ring", or "divalent group of condensed polycyclic aromatic" in the "divalent group of substituted or unsubstituted aromatic hydrocarbon", "divalent group of a substituted or unsubstituted aromatic heterocyclic ring", or "divalent group of substituted or unsubstituted condensed polycyclic aromatic" represented by A or B in general formula (1) include phenylene, biphenylylene, terphenylylene, tetrakisphenylene, naphthylene, anthrylene, phenanthrylene, fluorenylene, phenanthrolylene, indenylene, pyrenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, and acridinylene.

Specific examples of "substituent" in the "divalent group of substituted aromatic hydrocarbon", "divalent group of a substituted aromatic heterocyclic ring", or "divalent group of substituted condensed polycyclic aromatic" represented by A or B in general formula (1) include a deuterium atom, a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, pyrenyl, and pyridoindolyl. These substituents may be further substituted.

The compound of general formula (1) having a substituted anthracene ring structure and a pyridoindole ring structure of the present invention is a novel compound that has faster electron movement and superior hole blocking ability than conventional electron transport materials, and that remains thermally stable under high temperature conditions while having a stable thin-film state.

The compound of general formula (1) having a substituted anthracene ring structure and a pyridoindole ring structure of the present invention can be used as a constituent material of the electron injection layer and/or electron transport layer of an organic electroluminescent device (hereinafter, simply "organic EL device"). With the material having higher electron injectability and mobility than the conventional materials, the electron transport efficiency from the electron transport layer to the light emitting layer improves. This improves the luminous efficiency, and lowers driving voltage and thus improves the durability of the organic EL device.

The compound of general formula (1) having a substituted anthracene ring structure and a pyridoindole ring structure of the present invention also can be used as a constituent material of the hole blocking layer of an organic EL device. With the material having an excellent hole blocking ability and superior electron transportability and higher stability in the thin-film state than the conventional materials, the driving voltage lowers and the current resistance improves while maintaining high luminous efficiency. As a result, the maximum emission luminance of the organic EL device improves.

The compound of general formula (1) having a substituted anthracene ring structure and a pyridoindole ring structure of the present invention also can be used as a constituent material of the light emitting layer of an organic EL device. The material of the present invention has superior electron transportability and a wider band gap than the conventional materials, and can thus be used as the host material of the light emitting layer, and to form the light emitting layer by carrying a fluorescent material or phosphorescent material called a dopant. In this way, an organic EL device can be realized that has a low driving voltage and improved luminous efficiency.

The organic EL device of the present invention uses the compound having a substituted anthracene ring structure and a pyridoindole ring structure, wherein the compound has faster electron movement and superior hole blocking ability than the conventional electron transport materials, and remains thermally stable under high temperature conditions while having a stable thin-film state. In this way, high efficiency and high durability were realized.

Advantage of the Invention

The compound having a substituted anthracene ring structure and a pyridoindole ring structure of the present invention is useful as a constituent material of the electron injection layer, electron transport layer, hole blocking layer, or light emitting layer of an organic EL device. The compound has an excellent hole blocking ability, and excels in heat resistance while having a stable thin-film state. The organic EL device of the present invention has high luminous efficiency and high power efficiency, and can thus lower the actual driving voltage of the device. Further, the turn on voltage can be reduced to improve durability.

BRIEF DESCRIPTION OF THE DRAWINGS

FIG. 1 is a 1H-NMR chart of the compound of Example 1 of the present invention (Compound 9).
FIG. 2 is a 1H-NMR chart of the compound of Example 2 of the present invention (Compound 10).
FIG. 3 is a 1H-NMR chart of the compound of Example 3 of the present invention (Compound 42).
FIG. 4 is a 1H-NMR chart of the compound of Example 4 of the present invention (Compound 45).
FIG. 5 is a 1H-NMR chart of the compound of Example 5 of the present invention (Compound 52).
FIG. 6 is a 1H-NMR chart of the compound of Example 6 of the present invention (Compound 55).
FIG. 7 is a 1H-NMR chart of the compound of Example 7 of the present invention (Compound 59).
FIG. 8 is a 1H-NMR chart of the compound of Example 8 of the present invention (Compound 61).
FIG. 9 is a 1H-NMR chart of the compound of Example 9 of the present invention (Compound 87).
FIG. 10 is a 1H-NMR chart of the compound of Example 10 of the present invention (Compound 89).
FIG. 11 is a diagram illustrating the configuration of the EL devices of Examples 27 to 38.
FIG. 12 is a diagram illustrating the configuration of the EL device of Comparative Example 1.
FIG. 13 is a diagram illustrating the configuration of the EL device of Examples 39 to 44.
FIG. 14 is a diagram illustrating the configuration of the EL device of Comparative Example 2.

MODE FOR CARRYING OUT THE INVENTION

The compounds having a substituted anthracene ring structure and a pyridoindole ring structure of the present invention are novel compounds, and may be synthesized, for example, as follows. First, a corresponding halogenoanilinopyridine is subjected to a cyclization reaction using a palladium catalyst to synthesize a pyridoindole ring (see, for example, Non-Patent Document 5), and condensed with halides of various aromatic hydrocarbon compounds, condensed polycyclic aromatic compounds, or aromatic heterocyclic compounds to synthesize a compound having a corresponding pyridoindole ring structure. The compound having a corresponding pyridoindole ring structure is then subjected to a cross-coupling reaction, such as Suzuki coupling (see, for example, Non-Patent Document 7), with boronic acid or borate having an anthracene ring structure synthesized using a known method (see, for example, Non-Patent Document 6), so as to synthesize a compound having a substituted anthracene ring structure and a pyridoindole ring structure.

The following presents specific examples of preferred compounds among the compounds of general formula (1) having a substituted anthracene ring structure and a pyridoindole ring structure. The present invention, however, is not restricted to these compounds.

[Chemical Formula 2]

(Compound 2)

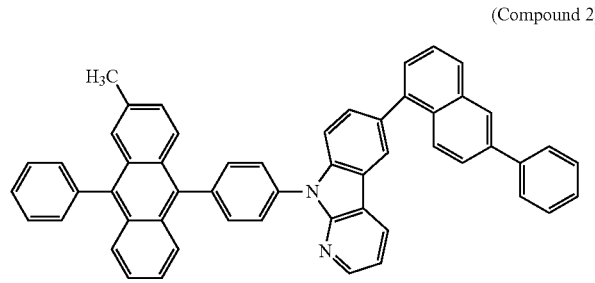

[Chemical Formula 3]

(Compound 3)

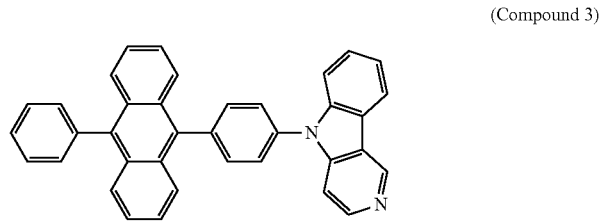

[Chemical Formula 4]

(Compound 4)

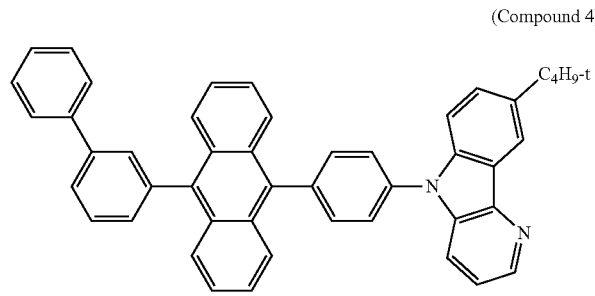

[Chemical Formula 5]

(Compound 5)

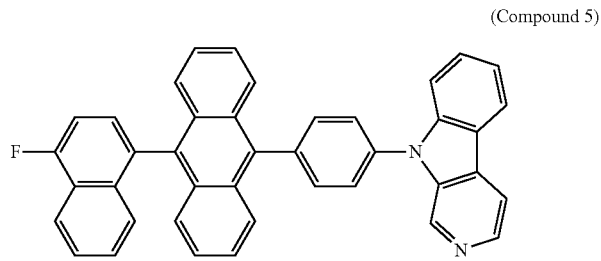

[Chemical Formula 6]

(Compound 6)

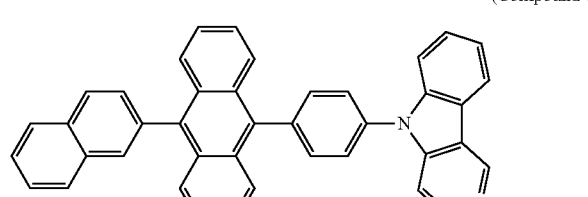

[Chemical Formula 7]

(Compound 7)

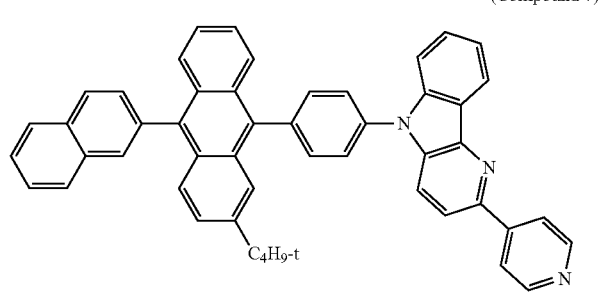

[Chemical Formula 8]

(Compound 8)

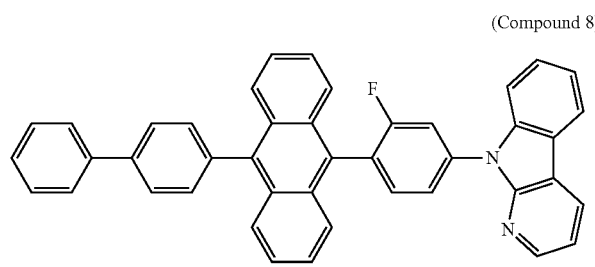

[Chemical Formula 9]

(Compound 9)

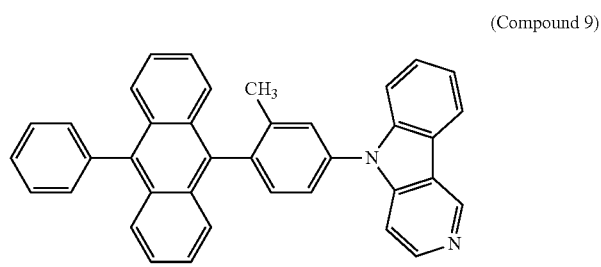

-continued
[Chemical Formula 10]
(Compound 10)
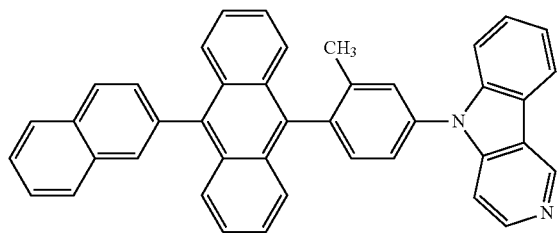
[Chemical Formula 11]
(Compound 11)
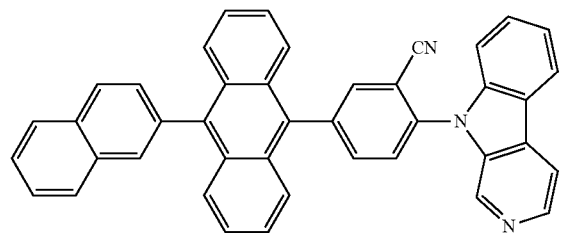
[Chemical Formula 12]
(Compound 12)
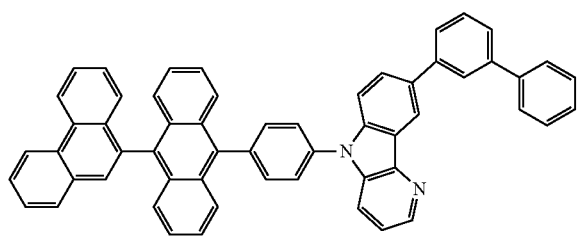
[Chemical Formula 13]
(Compound 13)
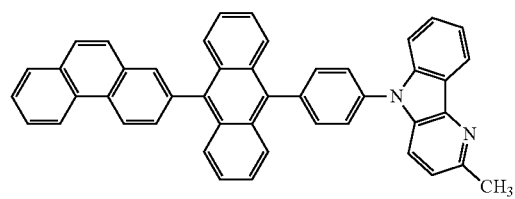
[Chemical Formula 14]
(Compound 14)
[Chemical Formula 15]
(Compound 15)
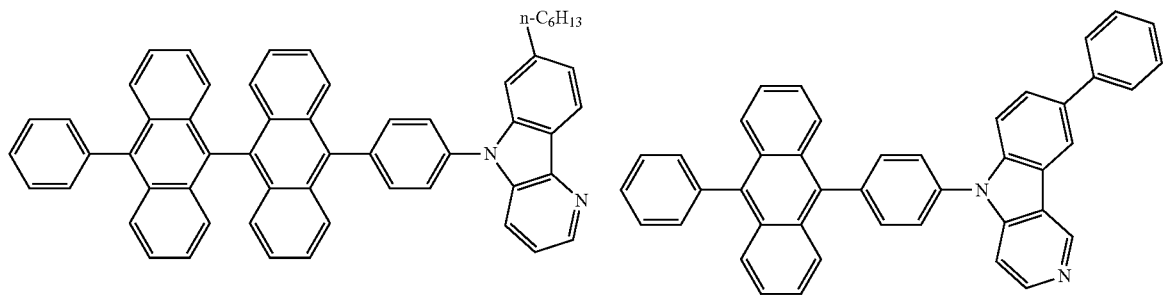
[Chemical Formula 16]
(Compound 16)
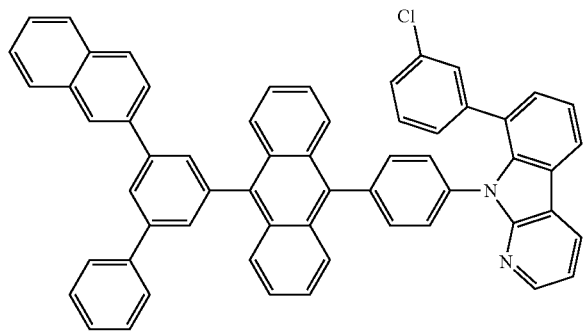
[Chemical Formula 17]
(Compound 17)
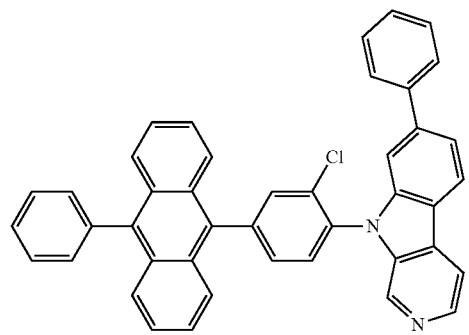

-continued
[Chemical Formula 18]
(Compound 18)
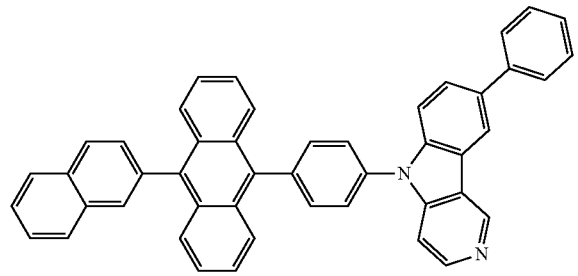
[Chemical Formula 19]
(Compound 19)
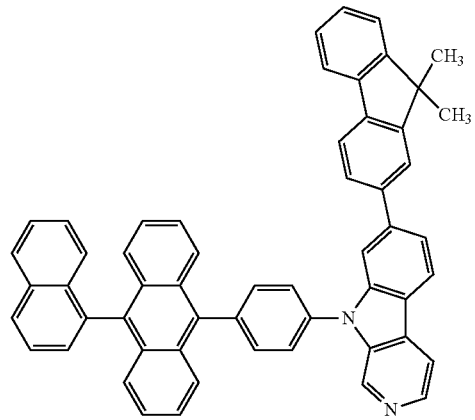
[Chemical Formula 20]
(Compound 20)
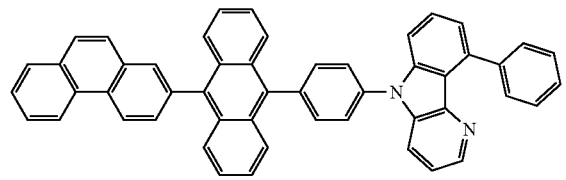
[Chemical Formula 21]
(Compound 21)
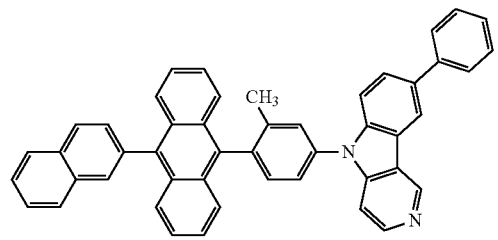
[Chemical Formula 22]
(Compound 22)
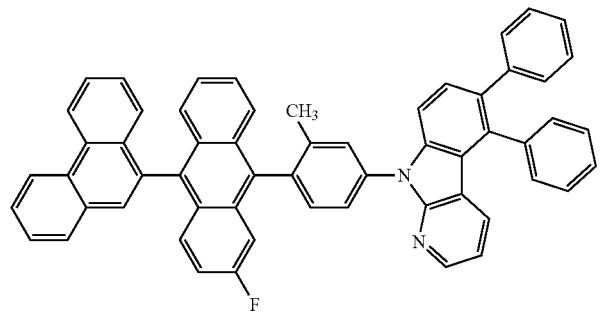
[Chemical Formula 23]
(Compound 23)
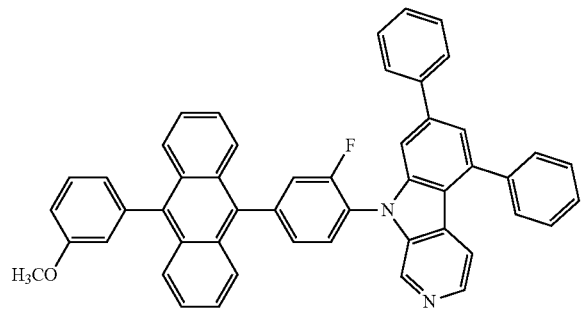
[Chemical Formula 24]
(Compound 24)
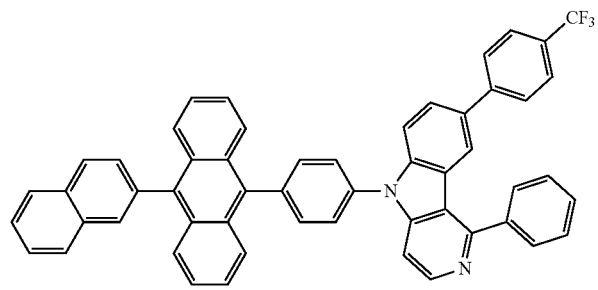
[Chemical Formula 25]
(Compound 25)
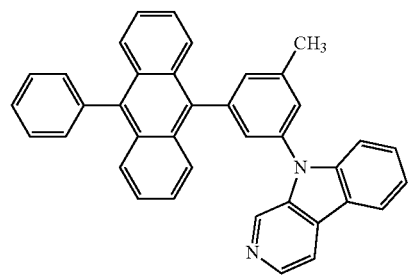

-continued
[Chemical Formula 26]
(Compound 26)
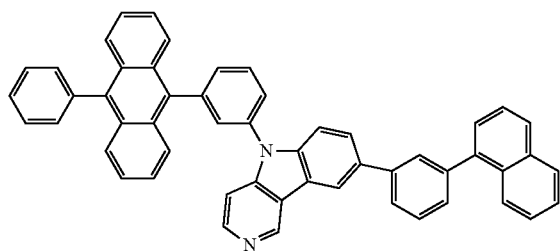
[Chemical Formula 27]
(Compound 27)
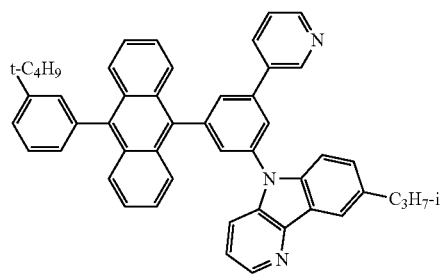
[Chemical Formula 28]
(Compound 28)
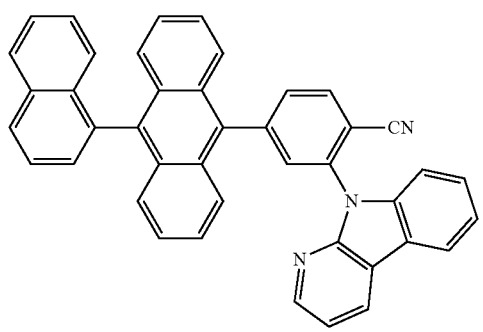
[Chemical Formula 29]
(Compound 29)
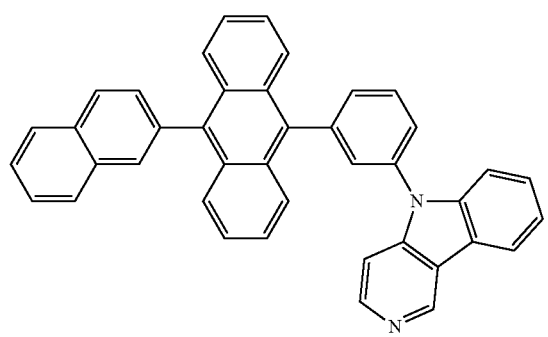
[Chemical Formula 30]
(Compound 30)
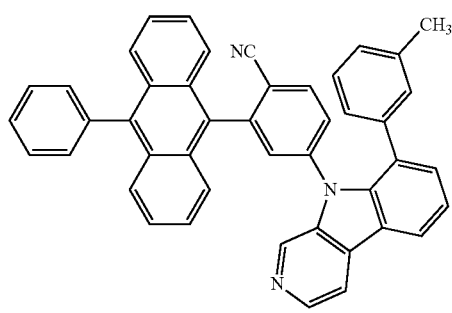
[Chemical Formula 31]
(Compound 31)
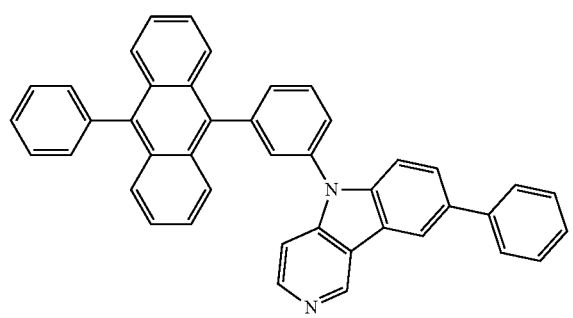
[Chemical Formula 32]
(Compound 32)
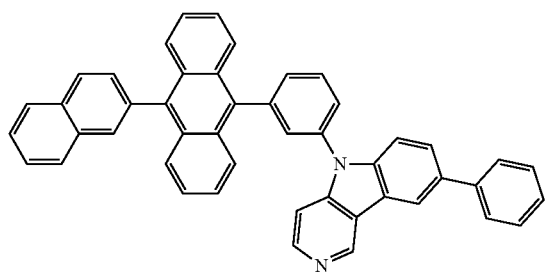
[Chemical Formula 33]
(Compound 33)
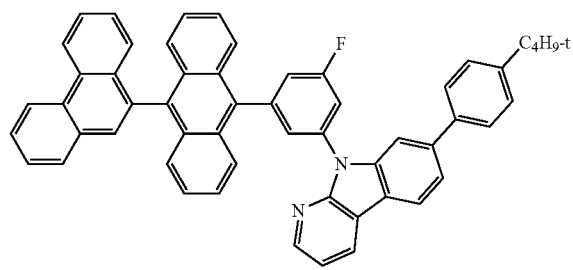

[Chemical Formula 34]
(Compound 34)
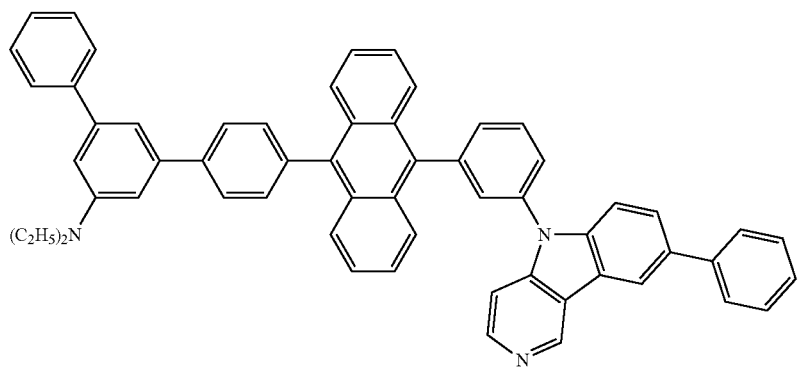
[Chemical Formula 35]
(Compound 35)
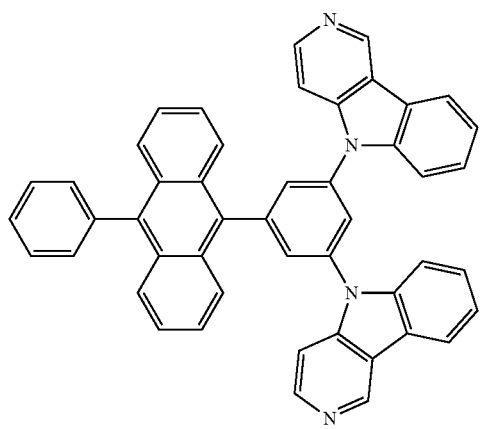
[Chemical Formula 36]
(Compound 36)
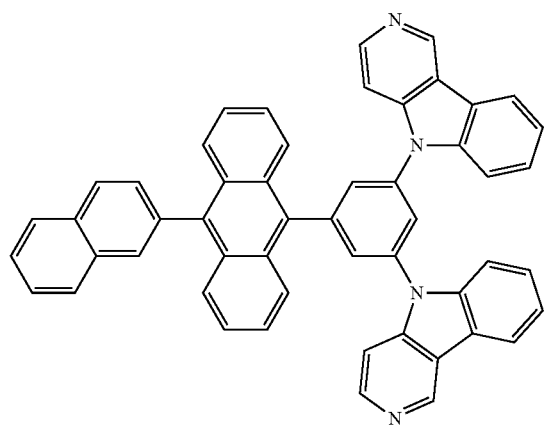
[Chemical Formula 37]
(Compound 37)
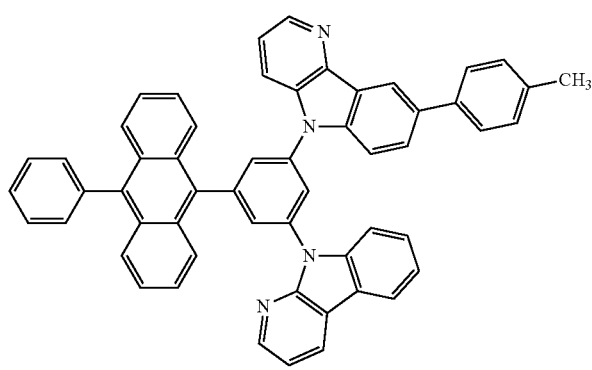
[Chemical Formula 38]
(Compound 38)
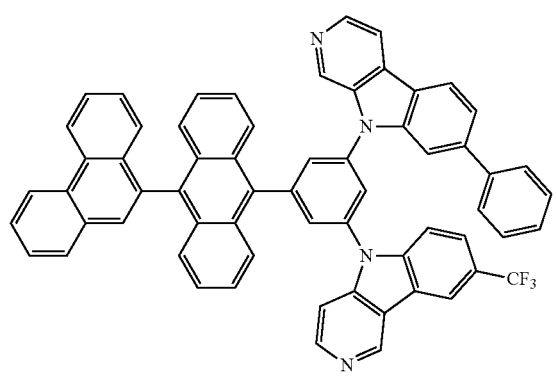

-continued
[Chemical Formula 39]
(Compound 39)
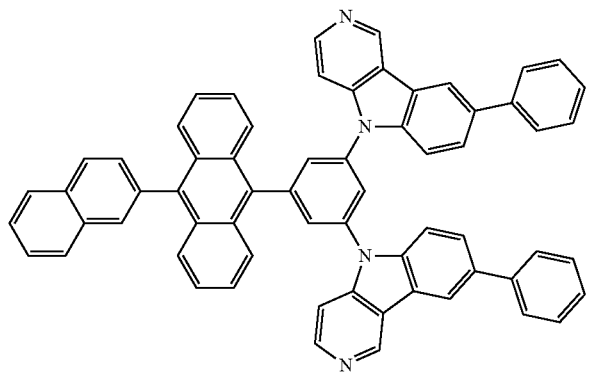
[Chemical Formula 40]
(Compound 40)
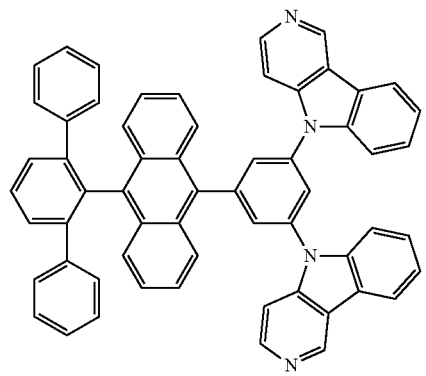
[Chemical Formula 41]
(Compound 41)
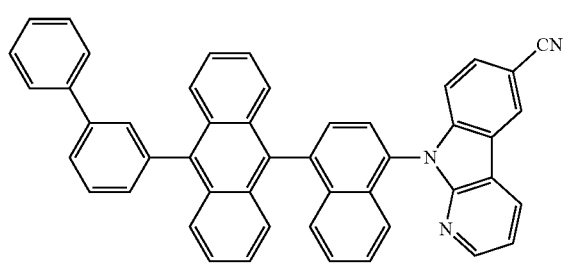
[Chemical Formula 42]
(Compound 42)
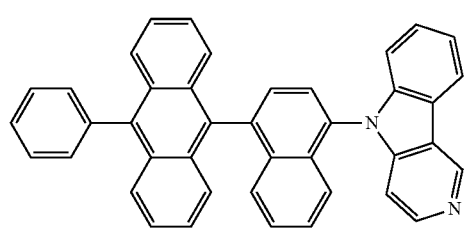
[Chemical Formula 43]
(Compound 43)
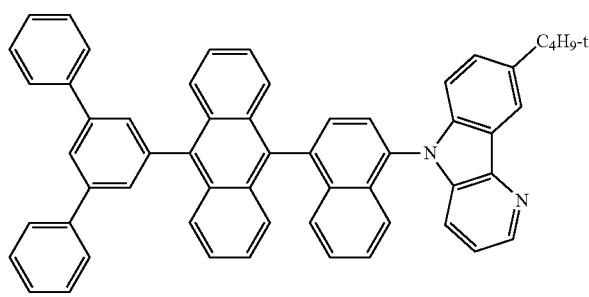
[Chemical Formula 44]
(Compound 44)
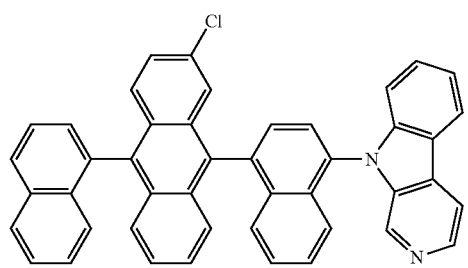
[Chemical Formula 45]
(Compound 45)
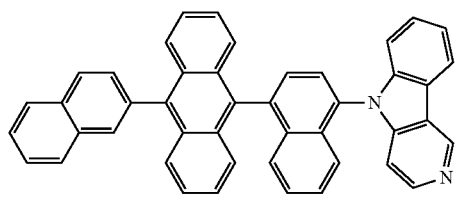
[Chemical Formula 46]
(Compound 46)
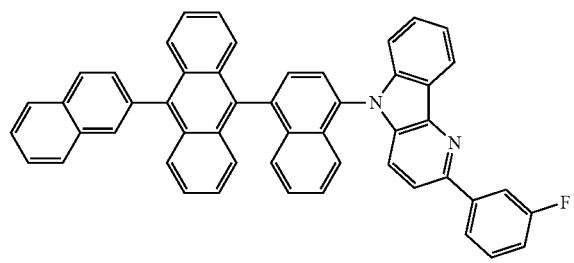

[Chemical Formula 47]
(Compound 47)
[Chemical Formula 48]
(Compound 48)
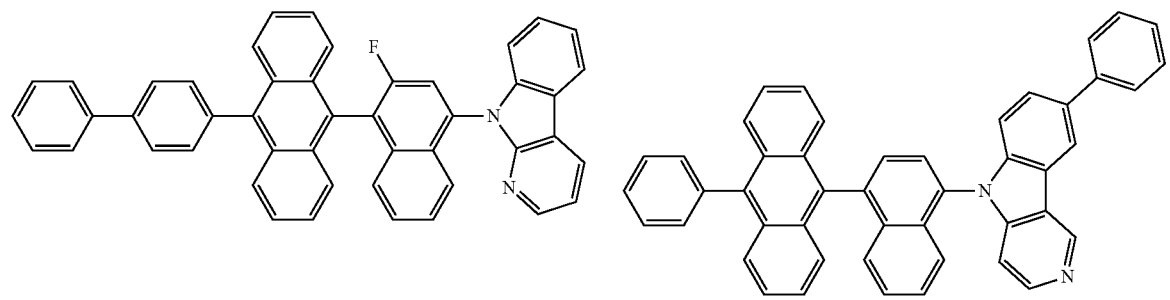
[Chemical Formula 49]
(Compound 49)
[Chemical Formula 50]
(Compound 50)
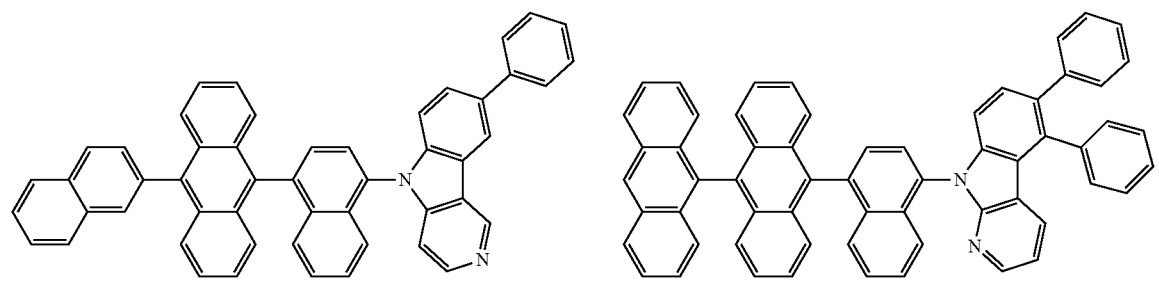
[Chemical Formula 51]
(Compound 51)
[Chemical Formula 52]
(Compound 52)
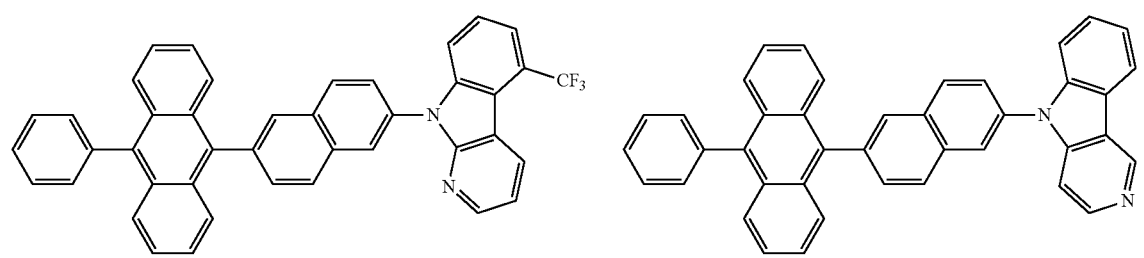
[Chemical Formula 53]
(Compound 53)
[Chemical Formula 54]
(Compound 54)
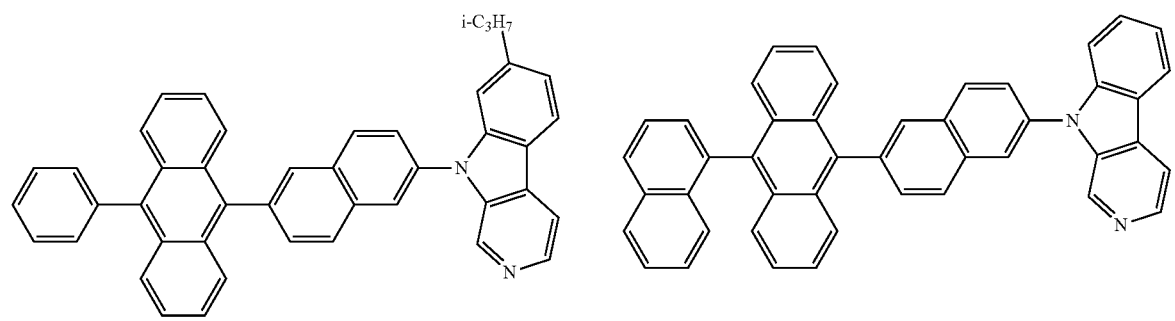

[Chemical Formula 55]
(Compound 55)
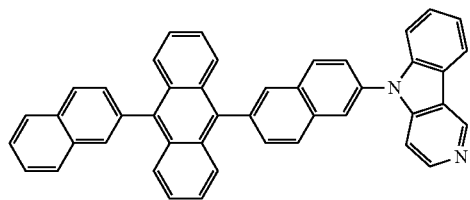
[Chemical Formula 56]
(Compound 56)
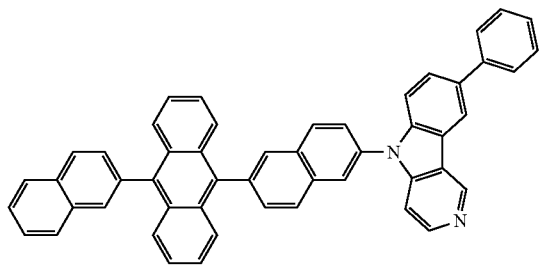
[Chemical Formula 57]
(Compound 57)
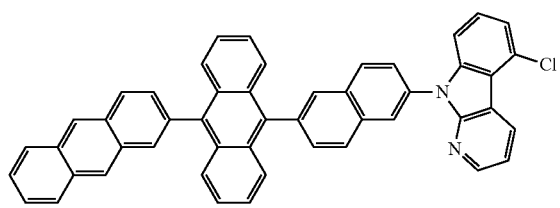
[Chemical Formula 58]
(Compound 58)
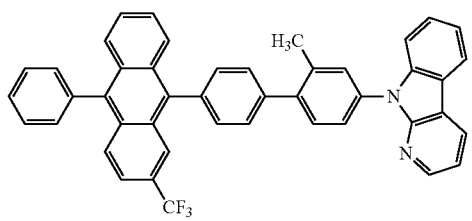
[Chemical Formula 59]
(Compound 59)
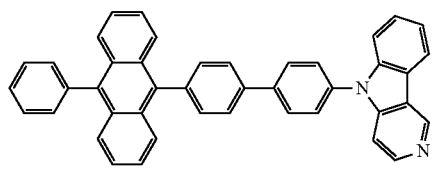
[Chemical Formula 60]
(Compound 60)
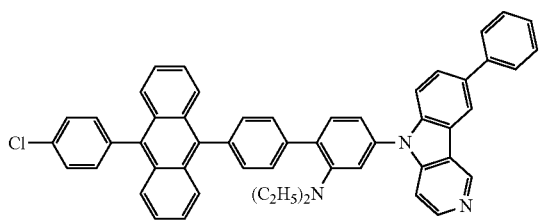
[Chemical Formula 61]
(Compound 61)
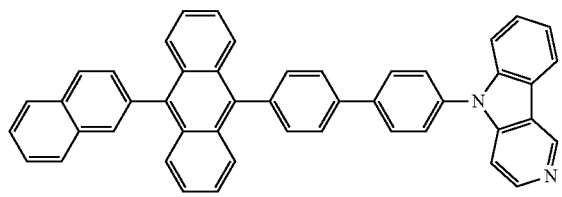
[Chemical Formula 62]
(Compound 62)
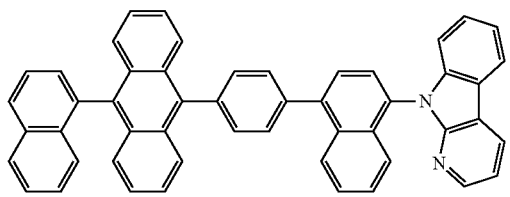
[Chemical Formula 63]
(Compound 63)
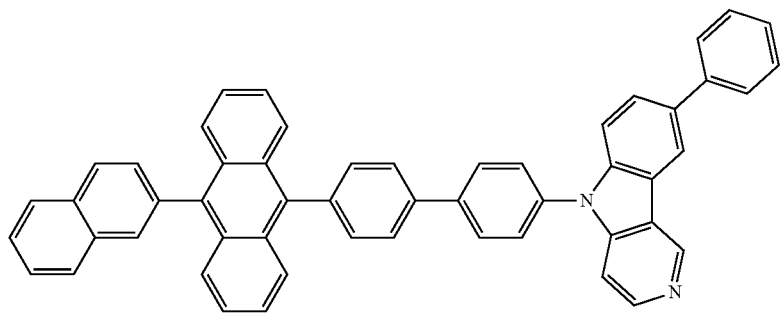

[Chemical Formula 64]
(Compound 64)
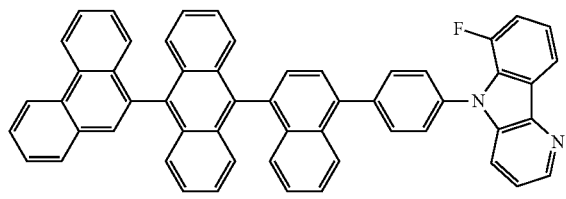
[Chemical Formula 65]
(Compound 65)
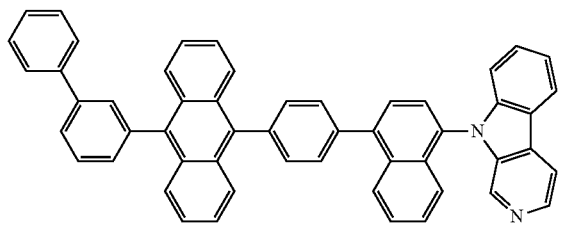
[Chemical Formula 66]
(Compound 66)
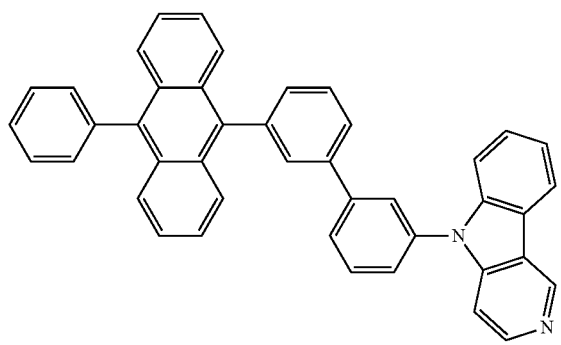
[Chemical Formula 67]
(Compound 67)
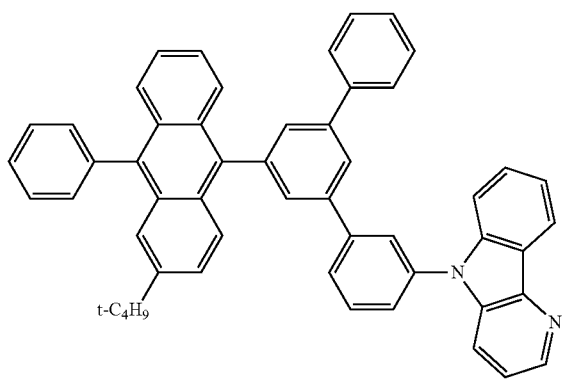
[Chemical Formula 68]
(Compound 68)
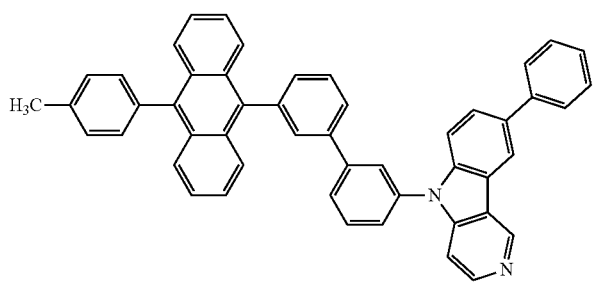
[Chemical Formula 69]
(Compound 69)
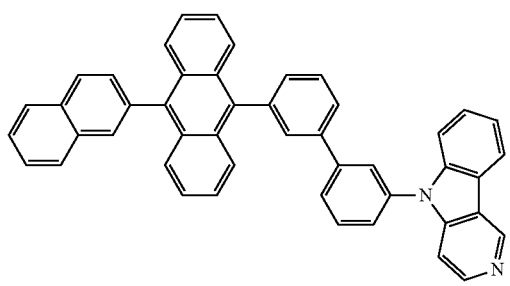
[Chemical Formula 70]
(Compound 70)
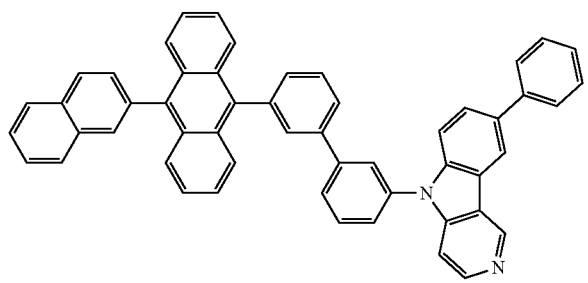
[Chemical Formula 71]
(Compound 71)
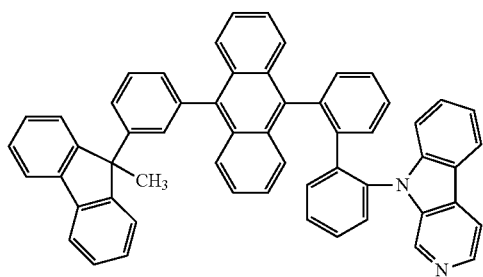

-continued
[Chemical Formula 72]
(Compound 72)
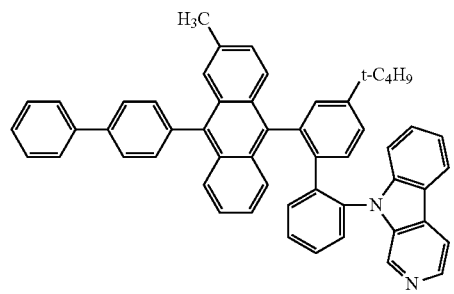
[Chemical Formula 73]
(Compound 73)
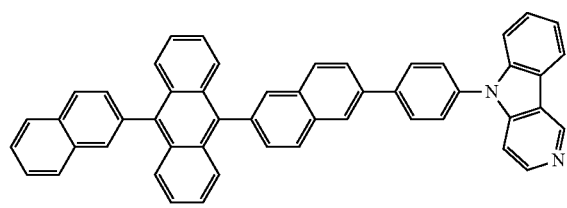
[Chemical Formula 74]
(Compound 74)
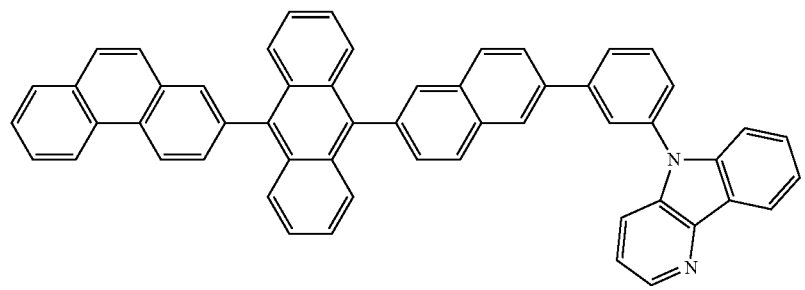
[Chemical Formula 75]
(Compound 75)
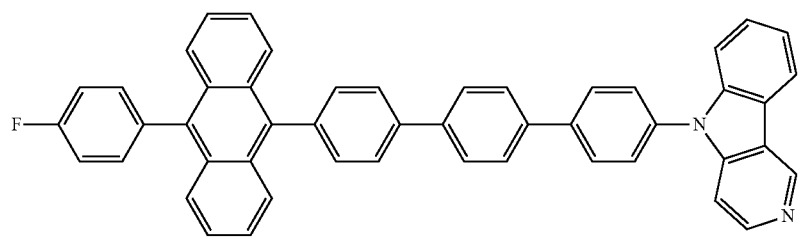
[Chemical Formula 76]
(Compound 76)
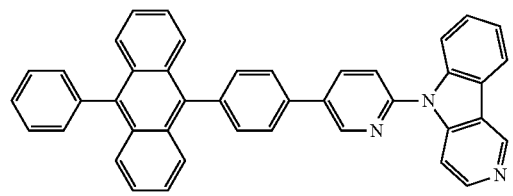
[Chemical Formula 77]
(Compound 77)
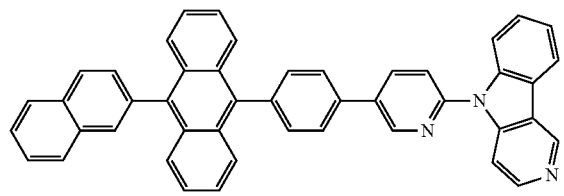
[Chemical Formula 78]
(Compound 78)
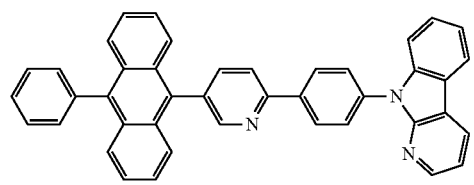
[Chemical Formula 79]
(Compound 79)
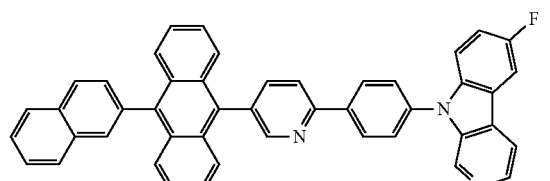

-continued
[Chemical Formula 80]
(Compound 80)
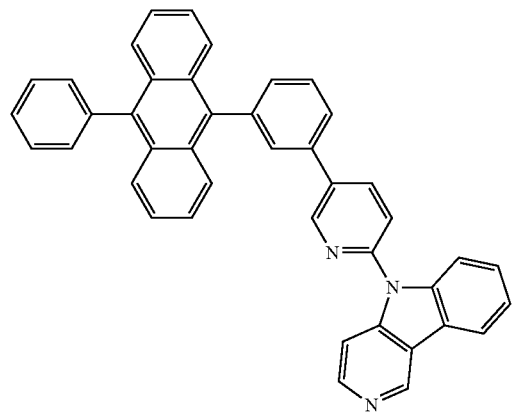
[Chemical Formula 81]
(Compound 81)
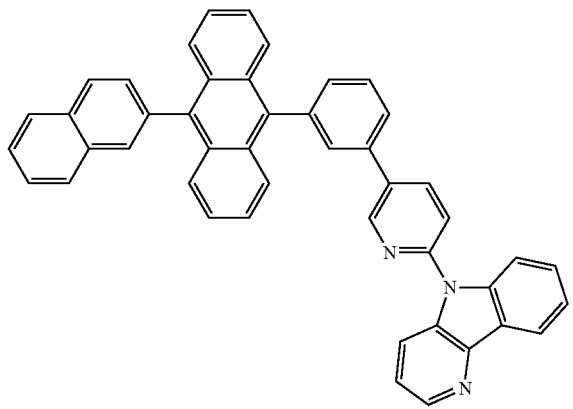
[Chemical Formula 82]
(Compound 82)
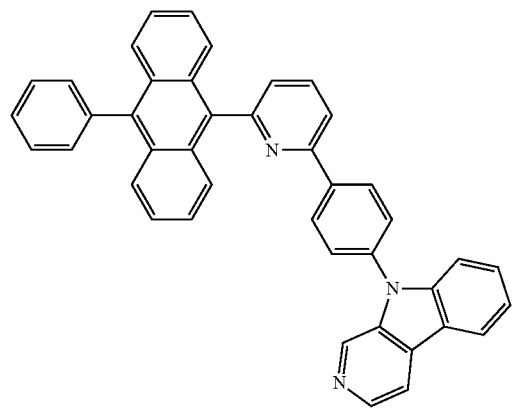
[Chemical Formula 83]
(Compound 83)
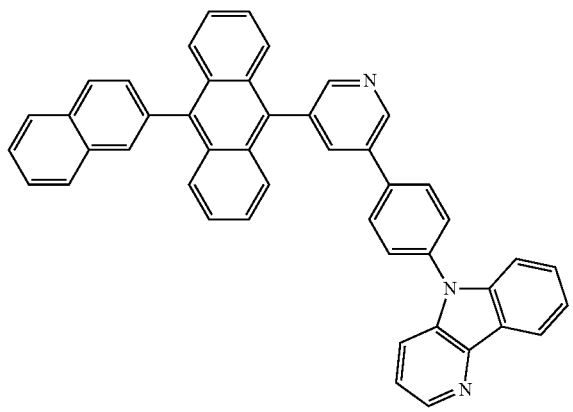
[Chemical Formula 84]
(Compound 84)
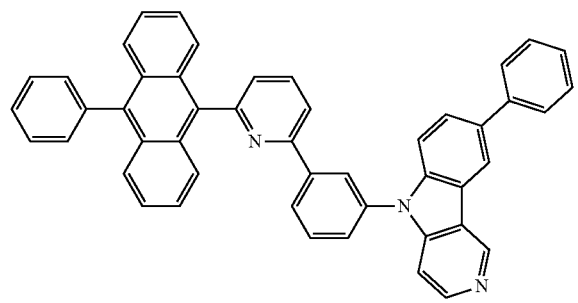
[Chemical Formula 85]
(Compound 85)
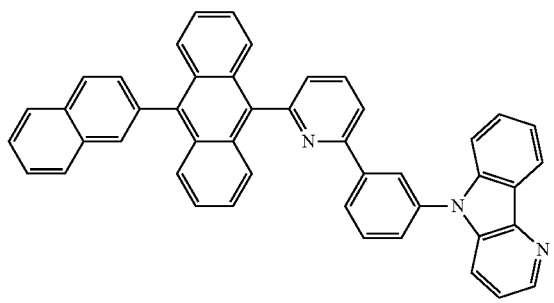

-continued
[Chemical Formula 86]
(Compound 86)
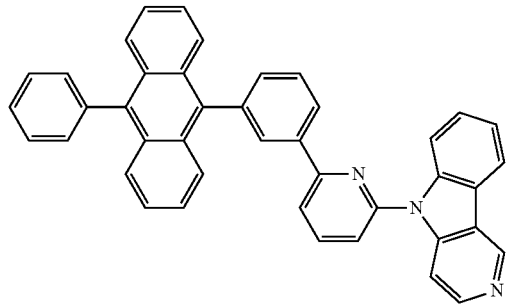
[Chemical Formula 87]
(Compound 87)
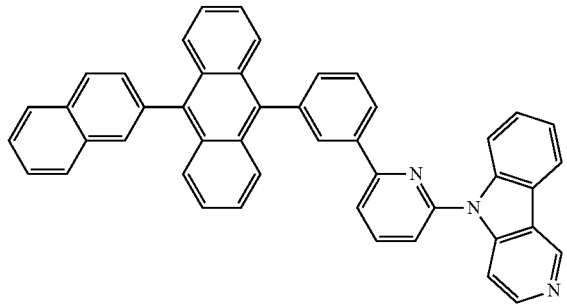
[Chemical Formula 88]
(Compound 88)
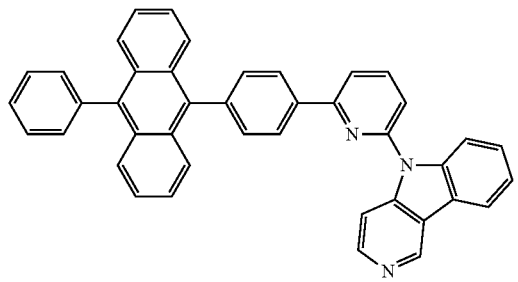
[Chemical Formula 89]
(Compound 89)
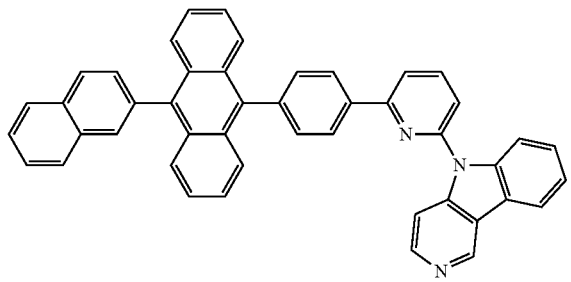
[Chemical Formula 90]
(Compound 90)
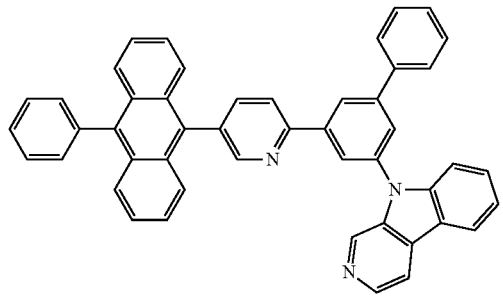
[Chemical Formula 91]
(Compound 91)
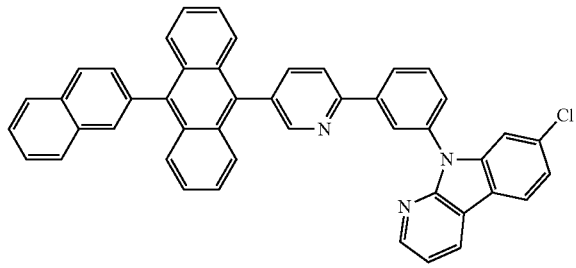
[Chemical Formula 92]
(Compound 92)
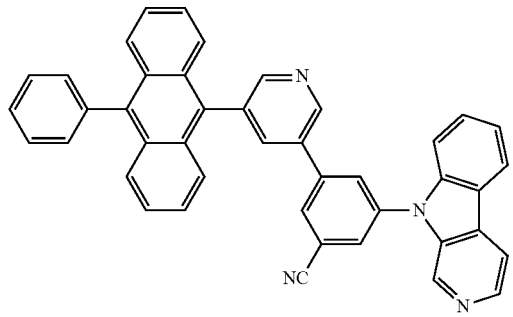
[Chemical Formula 93]
(Compound 93)
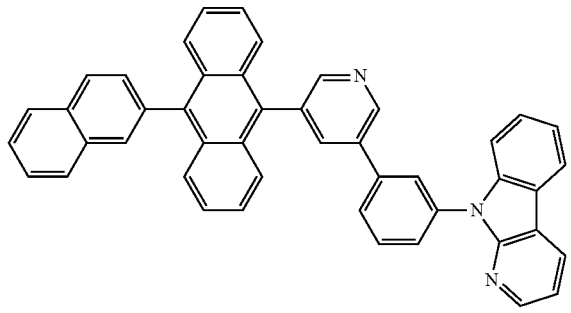

-continued
[Chemical Formula 94]
(Compound 94)
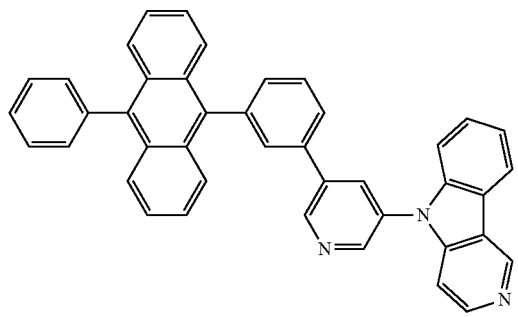
[Chemical Formula 95]
(Compound 95)
[Chemical Formula 96]
(Compound 96)
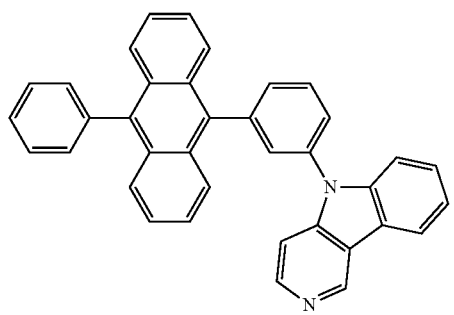
[Chemical Formula 97]
(Compound 97)
[Chemical Formula 98]
(Compound 98)
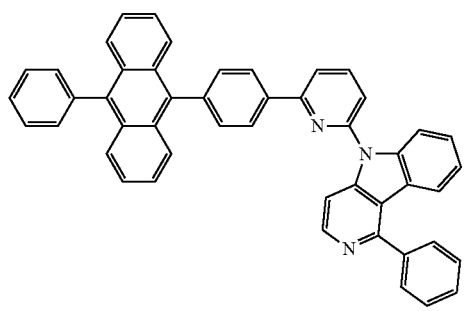
[Chemical Formula 99]
(Compound 99)
[Chemical Formula 100]
(Compound 100)
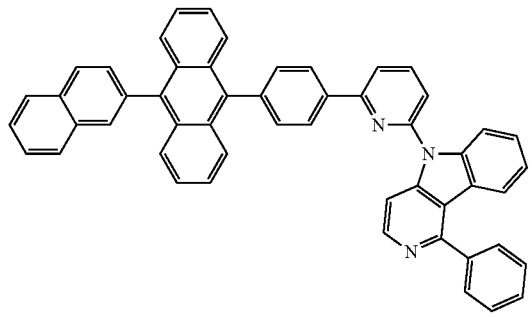
[Chemical Formula 101]
(Compound 101)
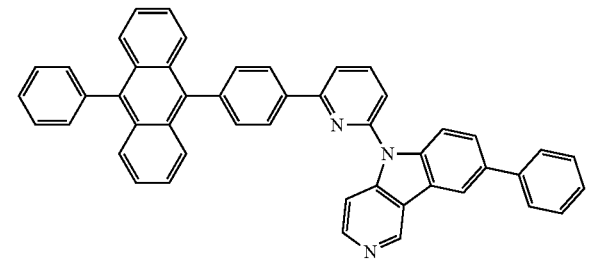

[Chemical Formula 102] (Compound 102)
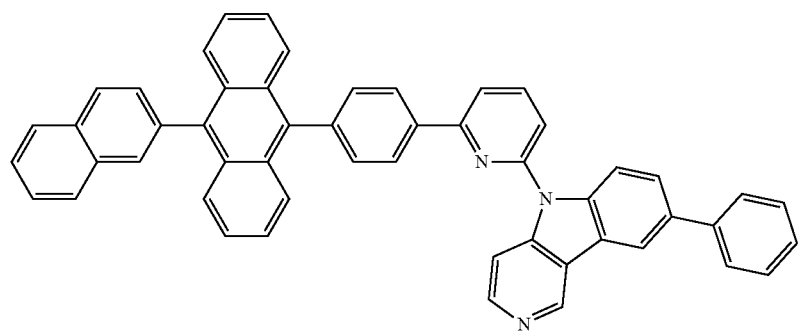
[Chemical Formula 103] (Compound 103)
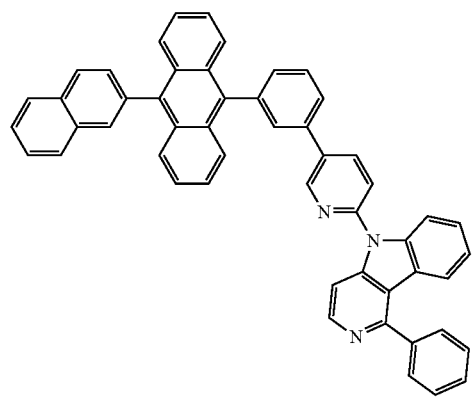
[Chemical Formula 104] (Compound 104)
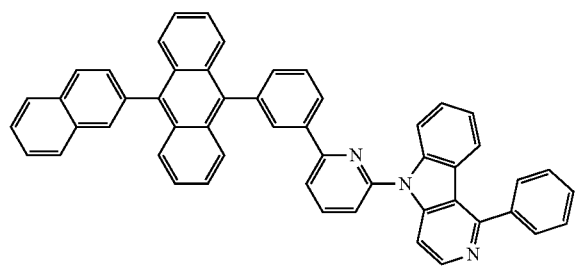
[Chemical Formula 105] (Compound 105)
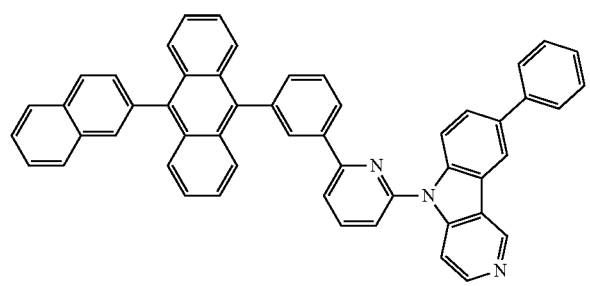
[Chemical Formula 106] (Compound 106)
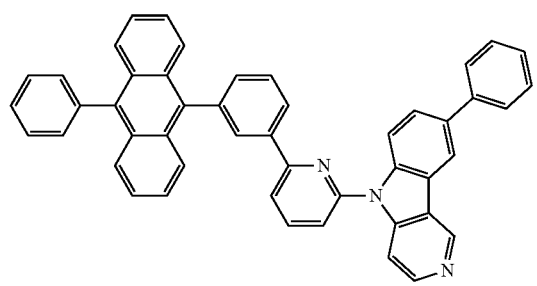
[Chemical Formula 107] (Compound 107)
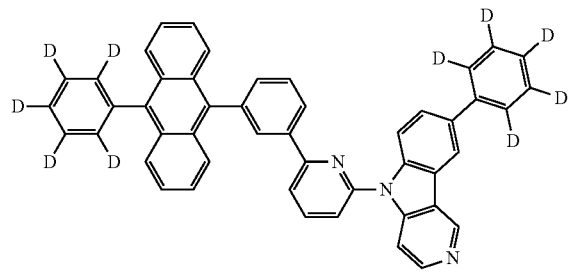
[Chemical Formula 108] (Compound 108)
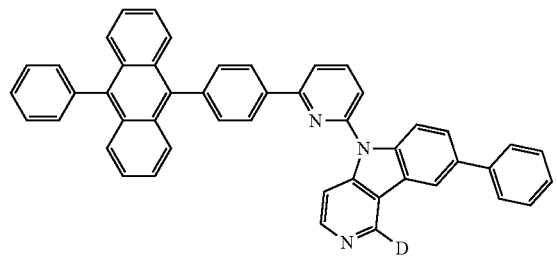

[Chemical Formula 109]
(Compound 109)
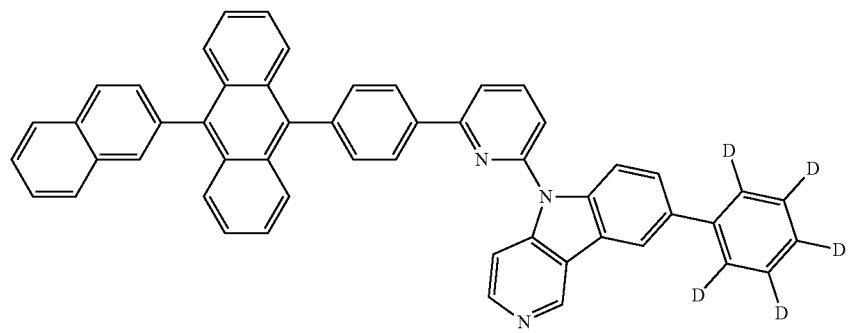
[Chemical Formula 110]
(Compound 110)
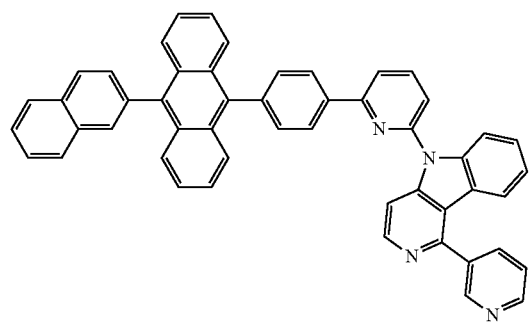
[Chemical Formula 111]
(Compound 111)
[Chemical Formula 112]
(Compound 112)
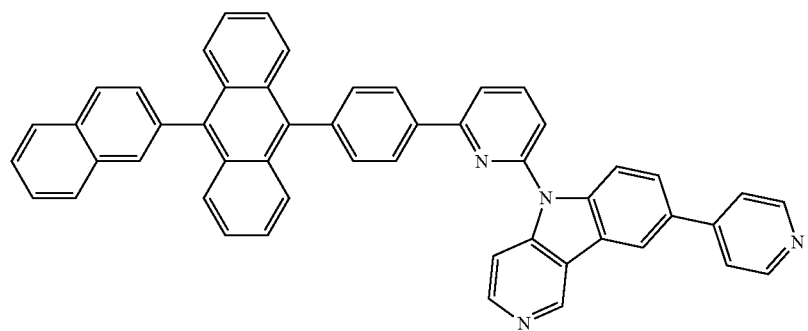
[Chemical Formula 113]
(Compound 113)
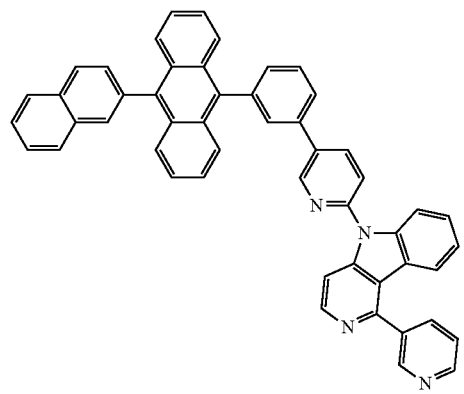
[Chemical Formula 114]
(Compound 114)
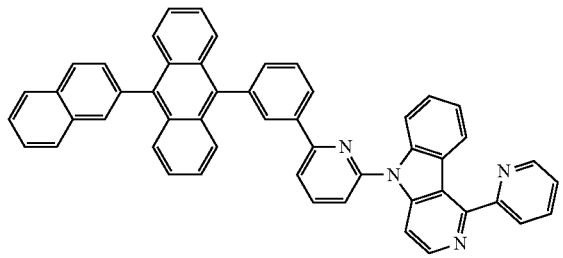

[Chemical Formula 115]

(Compound 115)

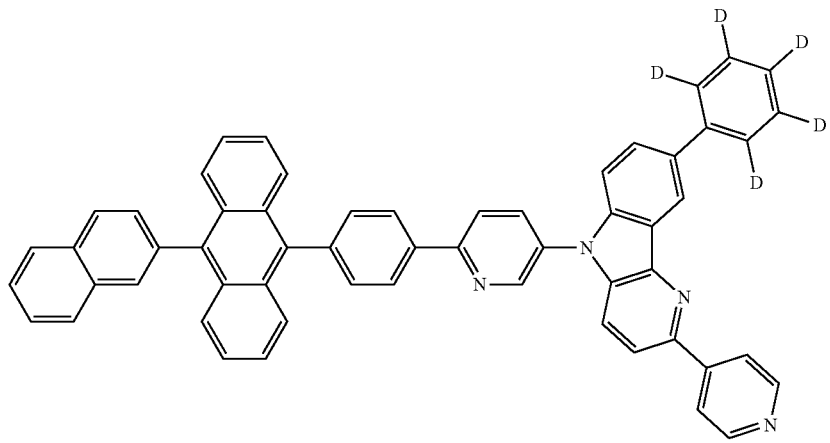

[Chemical Formula 116]

(Compound 116)

[Chemical Formula 117]

(Compound 117)

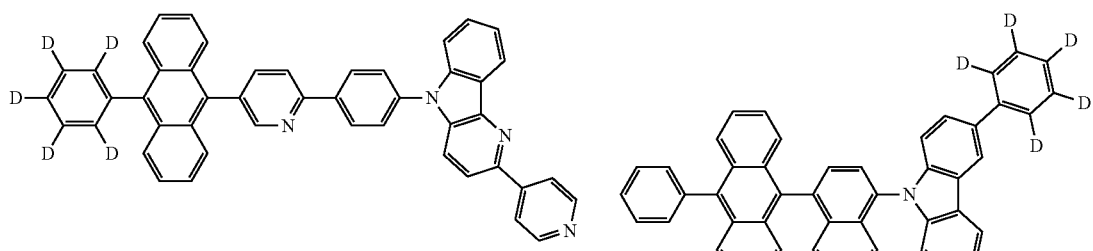

[Chemical Formula 118]

(Compound 118)

[Chemical Formula 119]

(Compound 119)

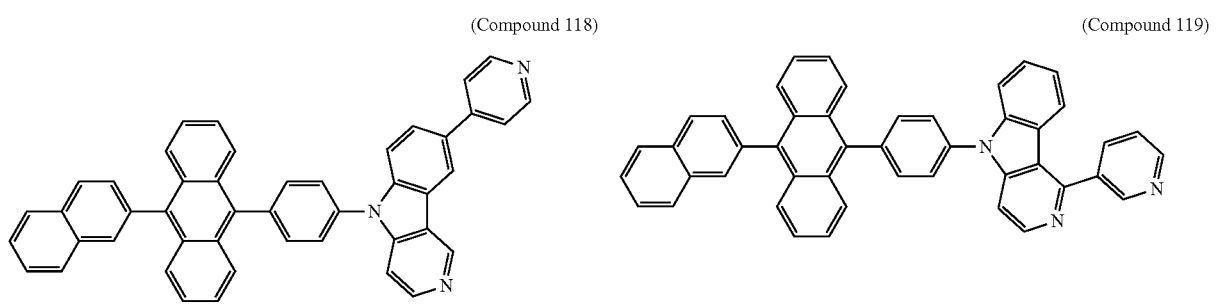

These compounds were purified by methods such as column chromatography, adsorption using, for example, a silica gel, activated carbon, or activated clay, and recrystallization or crystallization using a solvent. The compounds were identified by NMR analysis. Glass transition point (Tg) and melting point were taken for the measurement of physical properties. Melting point can be used as an index of vapor deposition, and glass transition point (Tg) as an index of stability in the thin-film state.

Melting point and glass transition point were measured using a powder, using a high-sensitive differential scanning calorimeter DSC3100S produced by Bruker AXS.

For the measurement of work function, a 100 nm-thick thin film was fabricated on an ITO substrate, and an atmosphere photoelectron spectrometer AC-3 produced by Riken Rad Co., Ltd. was used. The work function can be used as an index of hole blocking ability.

For the measurement of stability under high temperature conditions, the purity of samples prepared as a powder sealed under vacuum conditions was measured using an analytical device such as a high-performance liquid chromatography device before and after the samples were allowed to stand for one week in a constant-temperature vessel of a predetermined temperature, and changes in the purity of the samples were evaluated. Stability under high temperature conditions can be used as an index of the organic EL device durability during the fabrication or driving process.

The organic EL device of the present invention may have a structure including an anode, a hole transport layer, a light emitting layer, a hole blocking layer, an electron transport layer, and a cathode successively formed on a substrate, optionally with a hole injection layer between the anode and the hole transport layer, or with an electron injection layer between the electron transport layer and the cathode. In such multilayer structures, some of the organic layers may be omitted. For example, the device may be configured to include an anode, a hole transport layer, a light emitting layer, an electron transport layer, and a cathode successively formed on a substrate.

Electrode materials with a large work function, such as ITO and gold, are used as the anode of the organic EL device. The hole injection layer may be made of material such as copper phthalocyanine, starburst-type triphenylamine derivatives, various triphenylamine tetramers, and coating-type polymer materials.

Examples of the material used for the hole transport layer include benzidine derivatives such as N,N'-diphenyl-N,N'-di(m-tolyl)-benzidine (hereinafter, simply "TPD"), N,N'-diphenyl-N,N'-di(α-naphthyl)-benzidine (hereinafter, simply "NPD"), and N,N,N',N'-tetrabiphenylylbenzidine, and various triphenylamine tetramers. Examples of the material used for the hole injection/transport layer include coating-type polymer materials such as poly(3,4-ethylenedioxythiophene) (hereinafter, simply "PEDOT")/poly(styrene sulfonate) (hereinafter, simply "PSS").

Aside from the compounds having a substituted anthracene ring structure and a pyridoindole ring structure of the present invention, compounds having a hole blocking effect, including aluminum complexes, thiazole derivatives, oxazole derivatives, carbazole derivatives, polydialkylfluorene derivatives, phenanthroline derivatives such as BCP, and triazole derivatives such as TAZ may also be used for the light emitting layer, the hole blocking layer, and the electron transport layer of the organic EL device of the present invention.

A high-performance organic EL device can be fabricated by using conventional light-emitting materials such as aluminum complexes and styryl derivatives for the light emitting layer, and by using the compounds having a substituted anthracene ring structure and a pyridoindole ring structure of the present invention for the hole blocking layer or the electron transport layer. Phosphors, for example, such as quinacridone, coumalin, and rubrene may be used as the host material of the light emitting layer. Examples of phosphorescent material include green phosphorescent materials such as phenylpyridine iridium complex Ir(ppy)$_3$, blue phosphorescent materials such as FIrpic and FIr6, and red phosphorescent materials such as Btp$_2$Ir(acac). Here, the host material may be hole injecting and transporting host materials such as carbazole derivatives, including 4,4'-di(N-carbazolyl)biphenyl (hereinafter, simply "CBP"), 4,4',4"-tri(N-carbazolyl)triphenylamine (hereinafter, simply "TCTA"), and 1,3-bis(carbazol-9-yl)benzene (hereinafter, simply "mCP"). As electron transporting host material, material such as 2,2',2"-(1,3,5-phenylene)-tris(1-phenyl-1H-benzimidazole) (hereinafter, simply "TPBI") may be used. A high-performance organic EL device can be fabricated with the use of these materials.

Further, a conventional electron transporting material may be overlaid or co-vapor deposited on the compounds having a substituted anthracene ring structure and a pyridoindole ring structure of the present invention to form an electron transport layer.

The organic EL device of the present invention may include an electron injection layer. Material such as lithium fluoride may be used for the electron injection layer. The cathode may be made of electrode materials having a low work function (such as aluminum), or alloys of electrode materials having an even lower work function (such as aluminum-magnesium).

The following describes an embodiment of the present invention in more detail based on Examples. The present invention, however, is not restricted to the following Examples, as long as such departures are within the scope of the invention.

Example 1

Synthesis of 5-[3-methyl-4-(10-phenylanthracen-9-yl)phenyl]-5H-pyrido[4,3-b]indole (Compound 9)

5-(4-Bromo-3-methylphenyl)-5H-pyrido[4,3-b]indole (3.3 g), 9-(4,4,5,5-tetramethyl-[1,3,2]dioxabororan-2-yl)-10-phenylanthracene (3.7 g), tetrakis(triphenylphosphine)palladium (0.57 g), a 2 M potassium carbonate aqueous solution (24 ml), toluene (80 ml), and ethanol (20 ml) were added to a nitrogen-substituted reaction vessel, heated, and refluxed for 16 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene/hexane) to obtain a pale yellow powder of 5-[3-methyl-4-(10-phenylanthracen-9-yl)phenyl]-5H-pyrido[4,3-b]indole (Compound 9; 2.8 g; yield 56%).

The structure of the resulting pale yellow powder was identified by NMR. The 1H-NMR measurement result is presented in FIG. 1.

1H-NMR (CDCl$_3$) detected 26 hydrogen signals, as follows. δ (ppm)=9.45 (1H), 8.63 (1H), 8.27 (1H), 7.77 (2H), 7.71 (1H), 7.50-7.67 (12H), 7.44 (3H), 7.39 (2H), 2.06 (3H).

Example 2

Synthesis of 5-[3-methyl-4-{10-(naphthalen-2-yl)anthracen-9-yl}phenyl]-5H-pyrido[4,3-b]indole (Compound 10)

5-(4-Bromo-3-methylphenyl)-5H-pyrido[4,3-b]indole (2.4 g), 9-(4,4,5,5-tetramethyl-[1,3,2]dioxabororan-2-yl)-10-(naphthalen-2-yl)anthracene (3.7 g), tetrakis(triphenylphosphine)palladium (0.41 g), a 2 M potassium carbonate aqueous solution (18 ml), toluene (64 ml), and ethanol (16 ml) were added to a nitrogen-substituted reaction vessel, heated, and refluxed for 16 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene/cyclohexane) to obtain a pale yellow powder of 5-[3-methyl-4-{10-(naphthalen-2-yl)anthracen-9-yl}phenyl]-5H-pyrido[4,3-b]indole (Compound 10; 2.6 g; yield 65%).

The structure of the resulting pale yellow powder was identified by NMR. The 1H-NMR measurement result is presented in FIG. 2.

1H-NMR (CDCl$_3$) detected 28 hydrogen signals, as follows.

δ (ppm)=9.46 (1H), 8.63 (1H), 8.28 (1H), 8.10 (1H), 8.03 (2H), 7.94 (1H), 7.79 (2H), 7.72 (1H), 7.57-7.70 (10H), 7.45 (3H), 7.37 (2H), 2.08 (3H).

Example 3

Synthesis of 5-[4-(10-phenylanthracen-9-yl)naphthalen-1-yl]-5H-pyrido[4,3-b]indole (Compound 42)

5-(4-Bromonaphthalen-1-yl)-5H-pyrido[4,3-b]indole (3.1 g), 10-phenylanthracene-9-boronic acid (3.0 g), tetrakis(triphenylphosphine)palladium (0.48 g), a 2 M potassium carbonate aqueous solution (21 ml), toluene (70 ml), and ethanol (18 ml) were added to a nitrogen-substituted reaction vessel, heated, refluxed for 6 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by o-dichlorobenzene/ethyl acetate recrystallization to obtain a yellow powder of 5-[4-(10-phenylanthracen-9-yl)naphthalen-1-yl]-5H-pyrido[4,3-b]indole (Compound 42; 1.6 g; yield 36%).

The structure of the resulting yellow powder was identified by NMR. The 1H-NMR measurement result is presented in FIG. 3.

1H-NMR (CDCl$_3$) detected 26 hydrogen signals, as follows. δ (ppm)=9.53 (1H), 8.58 (1H), 8.35 (1H), 7.87 (1H), 7.80 (3H), 7.66 (2H), 7.61 (2H), 7.54 (4H), 7.47 (1H), 7.29-7.40 (9H), 7.20 (1H).

Example 4

Synthesis of 5-[4-{10-(naphthalen-2-yl)anthracen-9-yl}naphthalen-1-yl}-5H-pyrido[4,3-b]indole (Compound 45)

5-(4-Bromonaphthalen-1-yl)-5H-pyrido[4,3-b]indole (3.2 g), 9-(4,4,5,5-tetramethyl-[1,3,2]dioxabororan-2-yl)-10-(naphthalen-2-yl)anthracene (4.4 g), tetrakis(triphenylphosphine)palladium (0.50 g), a 2 M potassium carbonate aqueous solution (21 ml), toluene (70 ml), and ethanol (18 ml) were added to a nitrogen-substituted reaction vessel, heated, and refluxed for 9 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by toluene/hexane recrystallization to obtain a yellow powder of 5-[4-{10-(naphthalen-2-yl)anthracen-9-yl}naphthalen-1-yl]-5H-pyrido[4,3-b]indole (Compound 45; 1.7 g; yield 33%).

The structure of the resulting yellow powder was identified by NMR. The 1H-NMR measurement result is presented in FIG. 4.

1H-NMR (CDCl$_3$) detected 28 hydrogen signals, as follows.

δ (ppm)=9.53 (1H), 8.58 (1H), 8.35 (1H), 8.10 (3H), 7.96 (1H), 7.88 (1H), 7.83 (3H), 7.68-7.74 (1H), 7.63 (2H), 7.57 (2H), 7.53 (1H), 7.46 (1H), 7.30-7.40 (9H), 7.19 (1H).

Example 5

Synthesis of 5-[6-(10-phenylanthracen-9-yl)naphthalen-2-yl]-5H-pyrido[4,3-b]indole (Compound 52)

5-(6-Bromonaphthalen-2-yl)-5H-pyrido[4,3-b]indole (2.7 g), 9-(4,4,5,5-tetramethyl-[1,3,2]dioxabororan-2-yl)-10-phenylanthracene (3.3 g), tetrakis(triphenylphosphine)palladium (0.42 g), a 2 M potassium carbonate aqueous solution (18 ml), toluene (60 ml), and ethanol (15 ml) were added to a nitrogen-substituted reaction vessel, heated, and refluxed for 12 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by o-dichlorobenzene/ethyl acetate recrystallization to obtain a brownish white powder of 5-[6-(10-phenylanthracen-9-yl)naphthalen-2-yl]-5H-pyrido[4,3-b]indole (Compound 52; 1.5 g; yield 38%).

The structure of the resulting brownish white powder was identified by NMR. The 1H-NMR measurement result is presented in FIG. 5.

1H-NMR (CDCl$_3$) detected 26 hydrogen signals, as follows.

δ (ppm)=9.46 (1H), 8.59 (1H), 8.29 (1H), 8.22 (1H), 8.18 (2H), 8.14 (1H), 7.76 (6H), 7.52-7.65 (7H), 7.45 (2H), 7.37 (4H).

Example 6

Synthesis of 5-[6-{10-(naphthalen-2-yl)anthracen-9-yl}naphthalen-2-yl}-5H-pyrido[4,3-b]indole (Compound 55)

5-(6-Bromonaphthalen-2-yl)-5H-pyrido[4,3-b]indole (3.6 g), 9-(4,4,5,5-tetramethyl-[1,3,2]dioxabororan-2-yl)-10-(naphthalen-2-yl)anthracene (5.0 g), tetrakis(triphenylphosphine)palladium (0.56 g), a 2 M potassium carbonate aqueous solution (24 ml), toluene (80 ml), and ethanol (20 ml) were added to a nitrogen-substituted reaction vessel, heated, and refluxed for 12 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by o-dichlorobenzene/ethyl acetate recrystallization to obtain a yellowish green powder of 5-[6-{10-(naphthalen-2-yl)anthracen-9-yl}naphthalen-2-yl]-5H-pyrido[4,3-b]indole (Compound 55; 2.3 g; yield 40%).

The structure of the resulting yellowish green powder was identified by NMR. The 1H-NMR measurement result is presented in FIG. 6.

1H-NMR (CDCl$_3$) detected 28 hydrogen signals, as follows.

δ (ppm)=9.46 (1H), 8.60 (1H), 8.29 (1H), 8.23 (1H), 8.19 (3H), 8.11 (1H), 8.05 (1H), 8.03 (1H), 7.95 (1H), 7.78 (6H), 7.64 (4H), 7.56 (1H), 7.45 (2H), 7.36 (4H).

Example 7

Synthesis of 5-[4'-(10-phenylanthracen-9-yl)biphenyl-4-yl]-5H-pyrido[4,3-b]indole (Compound 59)

5-(4'-Bromobiphenyl-4-yl)-5H-pyrido[4,3-b]indole (3.5 g), 9-(4,4,5,5-tetramethyl-[1,3,2]dioxabororan-2-yl)-10-phenylanthracene (4.7 g), tetrakis(triphenylphosphine)palladium (0.51 g), a 2 M potassium carbonate aqueous solution (22 ml), toluene (112 ml), and ethanol (28 ml) were added to a nitrogen-substituted reaction vessel, heated, and refluxed for 8 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with toluene under heat to obtain a yellowish white powder of 5-[4'-(10-phenylanthracen-9-yl)biphenyl-4-yl]-5H-pyrido[4,3-b]indole (Compound 59; 3.1 g; yield 62%).

The structure of the resulting yellowish white powder was identified by NMR. The 1H-NMR measurement result is presented in FIG. 7.

1H-NMR (CDCl$_3$) detected 28 hydrogen signals, as follows.

δ (ppm)=9.43 (1H), 8.58 (1H), 8.26 (1H), 8.03 (2H), 7.94 (2H), 7.81 (2H), 7.72 (4H), 7.63 (4H), 7.50-7.58 (5H), 7.35-7.43 (6H).

Example 8

Synthesis of 5-[4'-{10-(naphthalen-2-yl)anthracen-9-yl]biphenyl-4-yl}-5H-pyrido[4,3-b]indole (Compound 61)

5-(4'-Bromobiphenyl-4-yl)-5H-pyrido[4,3-b]indole (3.2 g), 9-(4,4,5,5-tetramethyl-[1,3,2]dioxabororan-2-yl)-10-(naphthalen-2-yl)anthracene (5.2 g), tetrakis(triphenylphosphine)palladium (0.47 g), a 2 M potassium carbonate aqueous solution (20 ml), toluene (104 ml), and ethanol (26 ml) were added to a nitrogen-substituted reaction vessel, heated, and refluxed for 8 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with toluene under heat to obtain a yellowish white powder of 5-[4'-{10-(naphthalen-2-yl)anthracen-9-yl]biphenyl-4-yl}-5H-pyrido[4,3-b]indole (Compound 61; 2.5 g; yield 49%).

The structure of the resulting yellowish white powder was identified by NMR. The 1H-NMR measurement result is presented in FIG. 8.

1H-NMR (CDCl$_3$) detected 30 hydrogen signals, as follows.

δ (ppm)=9.43 (1H), 8.58 (1H), 8.26 (1H), 8.09 (1H), 8.02 (4H), 7.94 (3H), 7.83 (2H), 7.76 (2H), 7.71 (2H), 7.52-7.67 (7H), 7.37-7.43 (4H), 7.34 (2H).

Example 9

Synthesis of 5-[6-[3-{10-(naphthalen-2-yl)anthracen-9-yl}phenyl]pyridin-2-yl]-5H-pyrido[4,3-b]indole (Compound 87)

5-[6-(3-Bromophenyl)pyridin-2-yl]-5H-pyrido[4,3-b]indole (2.7 g), 9-(4,4,5,5-tetramethyl-[1,3,2]dioxabororan-2-yl)-10-(naphthalen-2-yl)anthracene (2.2 g), tetrakis(triphenylphosphine)palladium (0.32 g), a 2 M potassium carbonate aqueous solution (8 ml), toluene (16 ml), and ethanol (4 ml) were added to a nitrogen-substituted reaction vessel, heated, and refluxed for 9 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with ethyl acetate under heat to obtain a yellowish white powder of 5-[6-[3-{10-(naphthalen-2-yl)anthracen-9-yl}phenyl]pyridin-2-yl]-5H-pyrido[4,3-b]indole (Compound 87; 1.6 g; yield 47%).

The structure of the resulting yellowish white powder was identified by NMR. The 1H-NMR measurement result is presented in FIG. 9.

1H-NMR (CDCl$_3$) detected 29 hydrogen signals, as follows.

δ (ppm)=9.39 (1H), 8.56 (1H), 8.42 (1H), 8.26 (1H), 8.20 (1H), 8.09 (1H), 7.97-8.04 (4H), 7.93 (1H), 7.79-7.89 (5H), 7.74 (2H), 7.58-7.65 (5H), 7.51 (1H), 7.31-7.42 (5H).

Example 10

Synthesis of 5-[6-[4-{10-(naphthalen-2-yl)anthracen-9-yl]phenyl]pyridin-2-yl}-5H-pyrido[4,3-b]indole (Compound 89)

5-[6-(4-Bromophenyl)pyridin-2-yl]-5H-pyrido[4,3-b]indole (3.0 g), 9-(4,4,5,5-tetramethyl-[1,3,2]dioxabororan-2-yl)-10-(naphthalen-2-yl)anthracene (3.9 g), tetrakis(triphenylphosphine)palladium (0.43 g), a 2 M potassium carbonate aqueous solution (19 ml), toluene (60 ml), and ethanol (15 ml) were added to a nitrogen-substituted reaction vessel, heated, and refluxed for 11 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with ethyl acetate under heat to obtain a yellowish white powder of 5-[6-[4-{10-(naphthalen-2-yl)anthracen-9-yl]phenyl}pyridin-2-yl]-5H-pyrido[4,3-b]indole (Compound 89; 2.0 g; yield 42%).

The structure of the resulting yellowish white powder was identified by NMR. The 1H-NMR measurement result is presented in FIG. 10.

1H-NMR (CDCl$_3$) detected 29 hydrogen signals, as follows.

δ (ppm)=9.43 (1H), 8.65 (1H), 8.40 (2H), 8.25 (1H), 8.13 (1H), 8.09 (1H), 7.99-8.04 (4H), 7.92 (2H), 7.80 (2H), 7.74 (2H), 7.57-7.69 (7H), 7.45 (1H), 7.31-7.37 (4H).

Example 11

Synthesis of 5-[4-(10-phenylanthracen-9-yl)phenyl]-5H-pyrido[4,3-b]indole (Compound 3)

5-(4-Bromophenyl)-5H-pyrido[4,3-b]indole (2.5 g), 9-(4,4,5,5-tetramethyl-[1,3,2]dioxabororan-2-yl)-10-phenylanthracene (3.8 g), tetrakis(triphenylphosphine)palladium (0.45 g), a 2 M potassium carbonate aqueous solution (40 ml), toluene (240 ml), and ethanol (60 ml) were added to a nitrogen-substituted reaction vessel, heated, and refluxed for 16 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with toluene under heat to obtain a yellowish white powder of 5-[4-(10-phenylanthracen-9-yl)phenyl]-5H-pyrido[4,3-b]indole (Compound 3; 1.9 g; yield 49%).

The structure of the resulting yellowish white powder was identified by NMR.

1H-NMR (CDCl$_3$) detected 24 hydrogen signals, as follows.

δ (ppm)=9.45 (1H), 8.62 (1H), 8.28 (1H), 7.81 (4H), 7.76 (4H), 7.71 (1H), 7.63 (2H), 7.58 (3H), 7.51 (2H), 7.38-7.46 (5H).

Example 12

Synthesis of 5-[4-{10-(naphthalen-2-yl)anthracen-9-yl}phenyl]-5H-pyrido[4,3-b]indole (Compound 6)

5-(4-Bromophenyl)-5H-pyrido[4,3-b]indole (3.0 g), 9-(4,4,5,5-tetramethyl-[1,3,2]dioxabororan-2-yl)-10-(naphthalen-2-yl)anthracene (4.0 g), tetrakis(triphenylphosphine)palladium (0.54 g), a 2 M potassium carbonate aqueous solution (46 ml), toluene (240 ml), and ethanol (60 ml) were added to a nitrogen-substituted reaction vessel, heated, and refluxed for 10 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by being dispersed and washed with toluene under heat to obtain a yellow powder of 5-[4-{10-(naphthalen-2-yl)anthracen-9-yl}phenyl]-5H-pyrido[4,3-b]indole (Compound 6; 1.3 g; yield 26%).

The structure of the resulting yellow powder was identified by NMR.

1H-NMR (CDCl$_3$) detected 26 hydrogen signals, as follows.

δ (ppm)=9.46 (1H), 8.64 (1H), 8.29 (1H), 8.11 (1H), 8.05 (1H), 8.01 (1H), 7.94 (1H), 7.83 (4H), 7.79 (4H), 7.73 (1H), 7.57-7.65 (5H), 7.46 (3H), 7.37 (2H).

Example 13

Synthesis of 5-[4-(10-phenylanthracen-9-yl)phenyl]-8-phenyl-5H-pyrido[4,3-b]indole (Compound 15)

5-(4-Bromophenyl)-8-phenyl-5H-pyrido[4,3-b]indole (3.5 g), 10-phenylanthracene-9-boronic acid (3.1 g), tetrakis(triphenylphosphine)palladium (0.30 g), a 2 M potassium carbonate aqueous solution (21 ml), toluene (56 ml), and ethanol (14 ml) were added to a nitrogen-substituted reaction vessel, heated, and refluxed for 12 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene) to obtain a yellowish white powder of 5-[4-(10-phenylanthracen-9-yl)phenyl]-8-phenyl-5H-pyrido[4,3-b]indole (Compound 15; 3.3 g; yield 66%).

The structure of the resulting yellowish white powder was identified by NMR.

1H-NMR (CDCl$_3$) detected 28 hydrogen signals, as follows.

δ (ppm)=9.50 (1H), 8.65 (1H), 8.48 (1H), 7.83 (5H), 7.77 (7H), 7.63 (2H), 7.58 (2H), 7.52 (4H), 7.45 (2H), 7.39 (3H).

Example 14

Synthesis of 5-[4-{10-(naphthalen-2-yl)anthracen-9-yl}phenyl]-8-phenyl-5H-pyrido[4,3-b]indole (Compound 18)

5-(4-Bromophenyl)-8-phenyl-5H-pyrido[4,3-b]indole (3.2 g), 10-(naphthalen-2-yl)anthracene-9-boronic acid (3.4 g), tetrakis(triphenylphosphine)palladium (0.28 g), a 2 M potassium carbonate aqueous solution (18 ml), toluene (52 ml), and ethanol (13 ml) were added to a nitrogen-substituted reaction vessel, heated, and refluxed for 11 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene) to obtain a yellow powder of 5-[4-{10-(naphthalen-2-yl)anthracen-9-yl}phenyl]-8-phenyl-5H-pyrido[4,3-b]indole (Compound 18; 3.7 g; yield 74%).

The structure of the resulting yellow powder was identified by NMR.

1H-NMR (CDCl$_3$) detected 30 hydrogen signals, as follows.

δ (ppm)=9.51 (1H), 8.65 (1H), 8.49 (1H), 8.11 (1H), 8.05 (1H), 8.02 (1H), 7.94 (1H), 7.81 (12H), 7.62 (4H), 7.53 (2H), 7.46 (2H), 7.39 (3H).

Example 15

Synthesis of 5-[3-(10-phenylanthracen-9-yl)phenyl]-8-phenyl-5H-pyrido[4,3-b]indole (Compound 31)

5-(3-Bromophenyl)-8-phenyl-5H-pyrido[4,3-b]indole (3.2 g), 10-phenylanthracene-9-boronic acid (3.1 g), tetrakis(triphenylphosphine)palladium (0.31 g), a 2 M potassium carbonate aqueous solution (21 ml), toluene (56 ml), and ethanol (14 ml) were added to a nitrogen-substituted reaction vessel, heated, and refluxed for 7 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by toluene/hexane recrystallization to obtain a yellow powder of 5-[3-(10-phenylanthracen-9-yl)phenyl]-8-phenyl-5H-pyrido[4,3-b]indole (Compound 31; 3.6 g; yield 72%).

The structure of the resulting yellow powder was identified by NMR.

1H-NMR (CDCl$_3$) detected 28 hydrogen signals, as follows.

δ (ppm)=9.43 (1H), 8.55 (1H), 8.40 (1H), 7.90 (1H), 7.81 (3H), 7.74 (4H), 7.68 (4H), 7.61 (2H), 7.56 (1H), 7.43-7.50 (7H), 7.37 (3H).

Example 16

Synthesis of 5-[3-{10-(naphthalen-2-yl)anthracen-9-yl}phenyl]-8-phenyl-5H-pyrido[4,3-b]indole (Compound 32)

5-(3-Bromophenyl)-8-phenyl-5H-pyrido[4,3-b]indole (3.2 g), 10-(naphthalen-2-yl)anthracene-9-boronic acid (3.4 g), tetrakis(triphenylphosphine)palladium (0.28 g), a 2 M potassium carbonate aqueous solution (20 ml), toluene (52 ml), and ethanol (13 ml) were added to a nitrogen-substituted reaction vessel, heated, and refluxed for 7 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by toluene/methanol recrystallization to obtain a yellow powder of 5-[3-{10-(naphthalen-2-yl)anthracen-9-yl}phenyl]-8-phenyl-5H-pyrido[4,3-b]indole (Compound 32; 2.2 g; yield 44%).

The structure of the resulting yellow powder was identified by NMR.

1H-NMR (CDCl$_3$) detected 30 hydrogen signals, as follows.

δ (ppm)=9.44 (1H), 8.57 (1H), 8.42 (1H), 8.08 (1H), 8.02 (1H), 7.91 (2H), 7.85 (2H), 7.82 (1H), 7.75 (4H), 7.70 (4H), 7.60 (3H), 7.43-7.51 (6H), 7.36 (3H).

Example 17

Synthesis of 3,5-bis(5H-pyrido[4,3-b]indol-5-yl)-(10-phenylanthracen-9-yl)benzene (Compound 35)

3,5-Bis{5H-pyrido[4,3-b]indol-5-yl}-bromobenzene (3.7 g), 9-(4,4,5,5-tetramethyl-[1,3,2]dioxabororan-2-yl)-10-phenylanthracene (2.9 g), tetrakis(triphenylphosphine)palladium (0.44 g), a 2 M potassium carbonate aqueous solution (19 ml), toluene (72 ml), and ethanol (18 ml) were added to a nitrogen-substituted reaction vessel, heated, and refluxed for 21 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene/ethyl acetate) to obtain a yellow powder of 3,5-bis(5H-pyrido[4,3-b]indol-5-yl)-(10-phenylanthracen-9-yl)benzene (Compound 35; 2.9 g; yield 58%).

The structure of the resulting yellow powder was identified by NMR.

1H-NMR (CDCl$_3$) detected 30 hydrogen signals, as follows.

δ (ppm)=9.41 (2H), 8.60 (2H), 8.24 (2H), 8.05 (1H), 7.95 (2H), 7.91 (2H), 7.77 (4H), 7.53-7.64 (9H), 7.48 (2H), 7.43 (4H).

Example 18

Synthesis of 3,5-bis(5H-pyrido[4,3-b]indol-5-yl)-{10-(naphthalen-2-yl)anthracen-9-yl}benzene (Compound 36)

3,5-Bis{5H-pyrido[4,3-b]indol-5-yl}-bromobenzene (3.5 g), 9-(4,4,5,5-tetramethyl-[1,3,2]dioxabororan-2-yl)-10-(naphthalen-2-yl)anthracene (3.1 g), tetrakis(triphenylphosphine)palladium (0.41 g), a 2 M potassium carbonate aqueous solution (21 ml), toluene (72 ml), and ethanol (18 ml) were added to a nitrogen-substituted reaction vessel, heated, and refluxed for 17 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene) to obtain a yellow powder of 3,5-bis(5H-pyrido[4,3-b]indol-5-yl)-{10-(naphthalen-2-yl)anthracen-9-yl}benzene (Compound 36; 1.2 g; yield 24%).

The structure of the resulting yellow powder was identified by NMR.

1H-NMR (CDCl$_3$) detected 32 hydrogen signals, as follows.

δ (ppm)=9.43 (2H), 8.60 (2H), 8.25 (2H), 7.92-8.10 (9H), 7.78 (4H), 7.55-7.64 (9H), 7.39-7.45 (4H).

Example 19

Synthesis of 5-{5-[4-(10-phenylanthracen-9-yl)phenyl]pyridin-2-yl}-5H-pyrido[4,3-b]indole (Compound 76)

5-[5-(4-Bromophenyl)pyridin-2-yl]-5H-pyrido[4,3-b]indole (1.8 g), 10-phenylanthracene-9-boronic acid (1.3 g), tetrakis(triphenylphosphine)palladium (0.26 g), a 2 M potassium carbonate aqueous solution (7 ml), toluene (32 ml), and ethanol (8 ml) were added to a nitrogen-substituted reaction vessel, heated, and refluxed for 14 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by o-dichlorobenzene recrystallization to obtain a yellow powder of 5-{5-[4-(10-phenylanthracen-9-yl)phenyl]pyridin-2-yl}-5H-pyrido[4,3-b]indole (Compound 76; 1.0 g; yield 39%).

The structure of the resulting yellow powder was identified by NMR.

1H-NMR (CDCl$_3$) detected 27 hydrogen signals, as follows.

δ (ppm)=9.42 (1H), 9.14 (1H), 8.64 (1H), 8.32 (1H), 8.24 (1H), 7.92-7.97 (3H), 7.84 (1H), 7.73-7.80 (5H), 7.68 (2H), 7.56-7.63 (4H), 7.50 (2H), 7.35-7.45 (5H).

Example 20

Synthesis of 5-{5-[3-(10-phenylanthracen-9-yl)phenyl]pyridin-2-yl}-5H-pyrido[4,3-b]indole (Compound 80)

5-[5-(3-Bromophenyl)pyridin-2-yl]-5H-pyrido[4,3-b]indole (1.0 g), 10-phenylanthracene-9-boronic acid (1.0 g), tetrakis(triphenylphosphine)palladium (0.15 g), a 2 M potassium carbonate aqueous solution (4 ml), toluene (16 ml), and ethanol (4 ml) were added to a nitrogen-substituted reaction vessel, heated, and refluxed for 8 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by column chromatography (carrier: NH silica gel; eluent: toluene) to obtain a yellow powder of 5-{5-[3-(10-phenylanthracen-9-yl)phenyl]pyridin-2-yl}-5H-pyrido[4,3-b]indole (Compound 80; 1.1 g; yield 77%).

The structure of the resulting yellow powder was identified by NMR.

1H-NMR (CDCl$_3$) detected 27 hydrogen signals, as follows.

δ (ppm)=9.38 (1H), 9.06 (1H), 8.58 (1H), 8.23 (1H), 8.19 (1H), 7.88 (2H), 7.83 (1H), 7.72-7.82 (6H), 7.70 (1H), 7.48-7.65 (7H), 7.33-7.42 (5H).

Example 21

Synthesis of 5-{6-[3-(10-phenylanthracen-9-yl)phenyl]pyridin-2-yl}-5H-pyrido[4,3-b]indole (Compound 86)

5-[6-(3-Bromophenyl)pyridin-2-yl]-5H-pyrido[4,3-b]indole (2.5 g), 9-(4,4,5,5-tetramethyl-[1,3,2]dioxaboroan-2-yl)-10-phenylanthracene (2.7 g), tetrakis(triphenylphosphine)palladium (0.21 g), a 2 M potassium carbonate aqueous solution (9 ml), toluene (16 ml), and ethanol (4 ml) were added to a nitrogen-substituted reaction vessel, heated, and refluxed for 15 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by o-dichlorobenzene/ethyl acetate recrystallization to obtain a yellow powder of 5-[6-[3-(10-phenylanthracen-9-yl)phenyl]pyridin-2-yl]-5H-pyrido[4,3-b]indole (Compound 86; 2.2 g; yield 61%).

The structure of the resulting yellow powder was identified by NMR.

1H-NMR (CDCl$_3$) detected 27 hydrogen signals, as follows.

δ (ppm)=9.38 (1H), 8.55 (1H), 8.41 (1H), 8.23 (1H), 8.19 (1H), 7.99 (1H), 7.96 (1H), 7.85 (2H), 7.76-7.80 (3H), 7.72 (2H), 7.61 (3H), 7.56 (2H), 7.49 (3H), 7.33-7.40 (5H).

Example 22

Synthesis of 5-{6-[4-(10-phenylanthracen-9-yl)phenyl]pyridin-2-yl}-5H-pyrido[4,3-b]indole (Compound 88)

5-[6-(4-Bromophenyl)pyridin-2-yl]-5H-pyrido[4,3-b]indole (2.4 g), 9-(4,4,5,5-tetramethyl-[1,3,2]dioxaboroan-2-yl)-10-phenylanthracene (3.4 g), tetrakis(triphenylphosphine)palladium (0.35 g), a 2 M potassium carbonate aqueous solution (15 ml), toluene (48 ml), and ethanol (12 ml) were added to a nitrogen-substituted reaction vessel, heated, and refluxed for 12 hours while being stirred. The mixture was cooled to room temperature, and the deposit was collected by filtration. The deposit was dissolved under heat in o-dichlorobenzene, and, after removing the insolubles by filtration, the filtrate was concentrated under reduced pressure to obtain a crude product. The crude product was purified by o-dichlorobenzene/ethyl acetate recrystallization to obtain a yellowish white powder of 5-{6-[4-(10-phenylanthracen-9-yl)phenyl]pyridin-2-yl}-5H-pyrido[4,3-b]indole (Compound 88; 2.2 g; yield 64%).

The structure of the resulting yellowish white powder was identified by NMR.

1H-NMR (CDCl$_3$) detected 27 hydrogen signals, as follows.

δ (ppm)=9.42 (1H), 8.64 (1H), 8.39 (2H), 8.24 (1H), 8.12 (1H), 7.99-8.03 (2H), 7.90 (1H), 7.71-7.76 (4H), 7.57-7.66 (7H), 7.49 (2H), 7.44 (1H), 7.35 (4H).

Example 23

Synthesis of 5-[3-(10-phenylanthracen-9-yl)phenyl]-5H-pyrido[4,3-b]indole (Compound 96)

5-(3-Bromophenyl)-5H-pyrido[4,3-b]indole (1.7 g), 9-(4,4,5,5-tetramethyl-[1,3,2]dioxabororan-2-yl)-10-phenylanthracene (2.0 g), tetrakis(triphenylphosphine)palladium (0.30 g), a 2 M potassium carbonate aqueous solution (26 ml), toluene (160 ml), and ethanol (40 ml) were added to a nitrogen-substituted reaction vessel, heated, and refluxed for 20 hours while being stirred. The mixture was cooled to room temperature, and stirred after adding toluene (100 ml) and water (100 ml) to separate the organic layer. The organic layer was dehydrated with anhydrous magnesium sulfate, and concentrated under reduced pressure to obtain a crude product. The crude product was purified by toluene/hexane recrystallization to obtain a yellowish white powder of 5-[3-(10-phenylanthracen-9-yl)phenyl]-5H-pyrido[4,3-b]indole (Compound 96; 1.1 g; yield 42%).

The structure of the resulting yellow powder was identified by NMR.

1H-NMR (CDCl$_3$) detected 24 hydrogen signals, as follows.

δ (ppm)=9.39 (1H), 8.54 (1H), 8.22 (1H), 7.89 (1H), 7.80 (3H), 7.73 (3H), 7.55-7.67 (5H), 7.36-7.52 (9H).

Example 24

The melting point and glass transition point of the compounds of the present invention were determined using a high-sensitive differential scanning calorimeter (DSC 3100S produced by Bruker AXS).

|  | Melting point | Glass transition point |
|---|---|---|
| Compound of Example 1 of the present invention (Compound 9) | 286° C. | 132° C. |
| Compound of Example 2 of the present invention (Compound 10) | 316° C. | 157° C. |
| Compound of Example 3 of the present invention (Compound 42) | 376° C. | 164° C. |
| Compound of Example 4 of the present invention (Compound 45) | 317° C. | 182° C. |
| Compound of Example 5 of the present invention (Compound 52) | 398° C. | None |
| Compound of Example 6 of the present invention (Compound 55) | 434° C. | 140° C. |
| Compound of Example 7 of the present invention (Compound 59) | 404° C. | None |
| Compound of Example 8 of the present invention (Compound 61) | 409° C. | None |
| Compound of Example 9 of the present invention (Compound 87) | 269° C. | 150° C. |
| Compound of Example 10 of the present invention (Compound 89) | 310° C. | 159° C. |
| Compound of Example 11 of the present invention (Compound 3) | 299° C. | 130° C. |
| Compound of Example 12 of the present invention (Compound 6) | 280° C. | 155° C. |
| Compound of Example 13 of the present invention (Compound 15) | 330° C. | 148° C. |
| Compound of Example 14 of the present invention (Compound 18) | 312° C. | 164° C. |
| Compound of Example 15 of the present invention (Compound 31) | 292° C. | 134° C. |
| Compound of Example 16 of the present invention (Compound 32) | 306° C. | 152° C. |
| Compound of Example 17 of the present invention (Compound 35) | 359° C. | 173° C. |

-continued

|  | Melting point | Glass transition point |
|---|---|---|
| Compound of Example 18 of the present invention (Compound 36) | 412° C. | 192° C. |
| Compound of Example 19 of the present invention (Compound 76) | 339° C. | 140° C. |
| Compound of Example 20 of the present invention (Compound 80) | 165° C. | 138° C. |
| Compound of Example 21 of the present invention (Compound 86) | 286° C. | 132° C. |
| Compound of Example 22 of the present invention (Compound 88) | 331° C. | 149° C. |
| Compound of Example 23 of the present invention (Compound 96) | 265° C. | 115° C. |

The compounds of the present invention had glass transition points of 100° C. or higher, or did not show any recognizable glass transition point. These results suggest that the compounds of the present invention have a stable thin-film state.

Example 25

A 100 nm-thick vapor-deposited film was fabricated on an ITO substrate using the compounds of the present invention, and the work function was measured using an atmosphere photoelectron spectrometer (Model AC-3, produced by Riken Keiki Co., Ltd.).

|  | Work function |
|---|---|
| Compound of Example 1 of the present invention (Compound 9) | 5.89 eV |
| Compound of Example 2 of the present invention (Compound 10) | 5.94 eV |
| Compound of Example 3 of the present invention (Compound 42) | 5.91 eV |
| Compound of Example 4 of the present invention (Compound 45) | 5.96 eV |
| Compound of Example 5 of the present invention (Compound 52) | 5.96 eV |
| Compound of Example 6 of the present invention (Compound 55) | 5.90 eV |
| Compound of Example 7 of the present invention (Compound 59) | 5.90 eV |
| Compound of Example 8 of the present invention (Compound 61) | 5.91 eV |
| Compound of Example 9 of the present invention (Compound 87) | 5.89 eV |
| Compound of Example 10 of the present invention (Compound 89) | 5.80 eV |
| Compound of Example 11 of the present invention (Compound 3) | 5.89 eV |
| Compound of Example 12 of the present invention (Compound 6) | 6.34 eV |
| Compound of Example 13 of the present invention (Compound 15) | 5.92 eV |
| Compound of Example 14 of the present invention (Compound 18) | 5.91 eV |
| Compound of Example 15 of the present invention (Compound 31) | 5.99 eV |
| Compound of Example 16 of the present invention (Compound 32) | 6.01 eV |
| Compound of Example 17 of the present invention (Compound 35) | 6.24 eV |
| Compound of Example 18 of the present invention (Compound 36) | 6.36 eV |
| Compound of Example 19 of the present invention (Compound 76) | 5.89 eV |
| Compound of Example 20 of the present invention (Compound 80) | 5.99 eV |

-continued

|  | Work function |
|---|---|
| Compound of Example 21 of the present invention (Compound 86) | 5.92 eV |
| Compound of Example 22 of the present invention (Compound 88) | 5.92 eV |
| Compound of Example 23 of the present invention (Compound 96) | 5.96 eV |

As these results show, the compounds of the present invention have greater work functions than the work function 5.4 eV of common hole transport materials such as NPD and TPD, and thus possess a high hole blocking ability.

Example 26

The compounds of the present invention were used to perform a heat test for confirming stability under high temperature conditions. The heat test was performed as follows. The compounds of the present invention (10 mg each) were placed in a glass test tube, and the end of the glass test tube was sealed after creating a vacuum using a diaphragm pump. The sealed glass test tube was placed in a constant-temperature vessel of a predetermined temperature set to 300° C. to 350° C. The seal was removed after a 1-week static period to prepare test samples. Each sample was subjected to HPLC measurement before and after the heat test under the following conditions.

Measurement Conditions

Column: GL Sciences Inc., Inertsil ODS-SP, inner diameter 4.6 mm, length 250 mm

Eluent: acetonitrile/0.05% (v/v) trifluoroacetic acid aqueous solution=8/2 (v/v)

Flow rate: 1.0 ml/min

Column temperature: 40° C.

Measurement wavelength: 254 nm

The HPLC purity (peak area percentage, %) of the compound of the present invention in each sample was calculated from the resulting HPLC chart using a data processor. Samples with a purity decrease of less than 5% in terms of peak area percentage before and after the heat test were determined as "Good (with heat resistance)", and a purity decrease of 5% or more was determined as "Poor (no heat resistance)". The results of the heat test for each sample are as follows.

|  | Result of heat test | Test temperature |
|---|---|---|
| Compound of Example 1 of the present invention (Compound 9) | Good | 300° C. |
| Compound of Example 3 of the present invention (Compound 42) | Good | 350° C. |
| Compound of Example 4 of the present invention (Compound 45) | Good | 330° C. |
| Compound of Example 5 of the present invention (Compound 52) | Good | 350° C. |
| Compound of Example 6 of the present invention (Compound 55) | Good | 350° C. |
| Compound of Example 8 of the present invention (Compound 61) | Good | 350° C. |
| Compound of Example 9 of the present invention (Compound 87) | Good | 330° C. |
| Compound of Example 10 of the present invention (Compound 89) | Good | 340° C. |
| Compound of Example 22 of the present invention (Compound 88) | Good | 340° C. |
| BCP (Comparative Compound) | Poor | 300° C. |

As can be seen from these results, the compounds of the present invention are stable, as demonstrated by a purity decrease of less than 5% in terms of peak area percentage under high temperature conditions. On the other hand, a purity decrease in terms of peak area percentage was 5% or more in Comparative Compound BCP (Compound 120 with the structural formula below). It can be said from this that the compounds of the present invention have superior heat resistance.

[Chemical Formula 120]

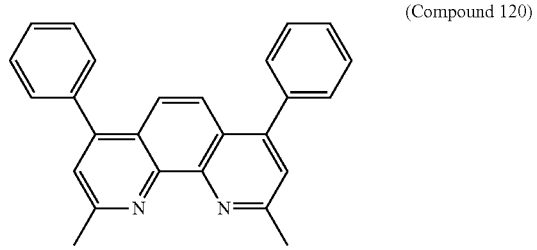

(Compound 120)

Example 27

The organic EL device, as illustrated in FIG. 11, was fabricated from a hole injection layer 3, a hole transport layer 4, a light emitting layer 5, a hole blocking layer 6, an electron transport layer 7, an electron injection layer 8, a cathode (aluminum electrode) 9 successively formed by vapor deposition on a glass substrate 1 that had been provided beforehand with an ITO electrode as a transparent anode 2.

[Chemical Formula 121]

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming Compound 121 of the structural formula below over the transparent anode 2 in a thickness of 20 nm at a deposition rate of 6 nm/min. The hole transport layer 4 was then formed on the hole injection layer 3 by forming Compound 122 of the structural formula below in a thickness of 40 nm at a deposition rate of 6 nm/min. Thereafter, the light emitting layer 5 was formed on the hole transport layer 4 by forming Compounds 123 and 124 of the structural formulae below in a thickness of 30 nm using dual vapor deposition at a deposition rate ratio of compound 123: compound 124=5:95. The hole blocking layer-electron transport layer 6 and 7 were then formed on the light emitting layer 5 by forming the compound of Example 1 of the present invention (Compound 9) in a thickness of 30 nm at a deposition rate of 6 nm/min. Then, the electron injection layer 8 was formed on the hole blocking layer-electron transport layer 6 and 7 by forming lithium fluoride in a thickness of 0.5 nm at a deposition rate of 0.6 nm/min Finally, the cathode 9 was formed by vapor depositing aluminum in a thickness of 150 nm. The characteristics of the organic EL device thus fabricated were measured in an atmosphere at ordinary temperature.

Table 1 summarizes the results of the emission characteristics measurements performed by applying a DC voltage to the organic EL device fabricated with the compound of Example 1 of the present invention (Compound 9).

(Compound 121)

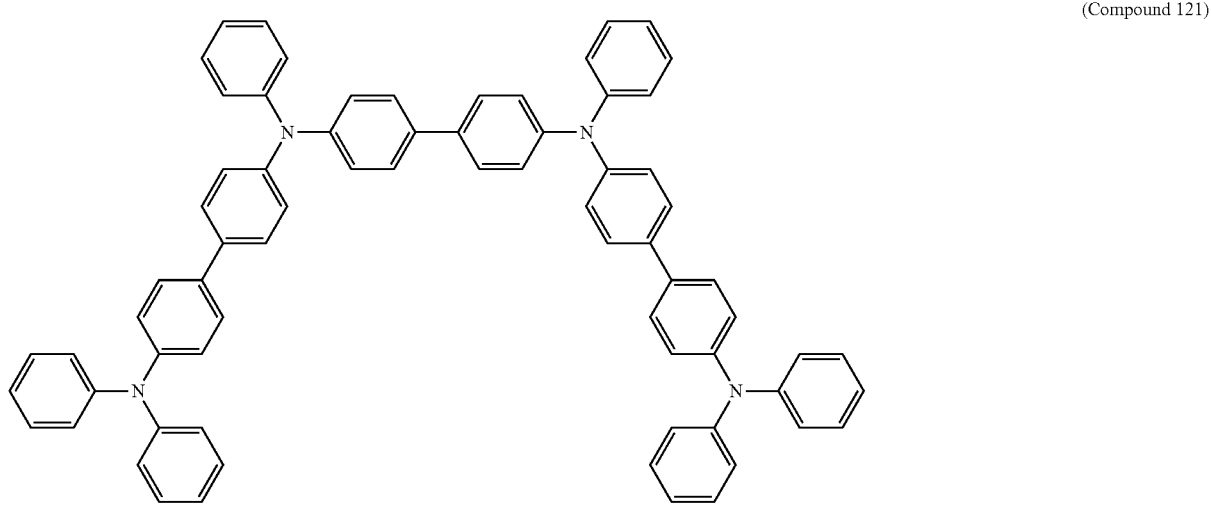

-continued

[Chemical Formula 122]

(Compound 122)

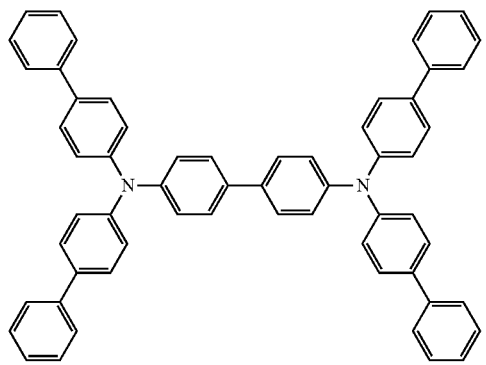

[Chemical Formula 123]

(Compound 123)

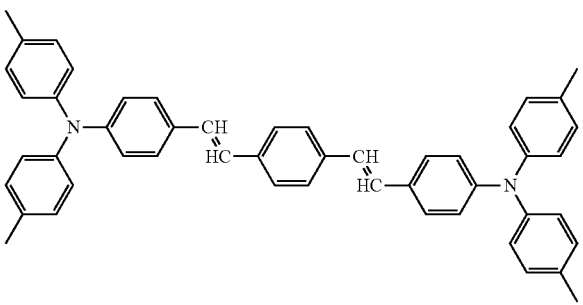

[Chemical Formula 124]

(Compound 124)

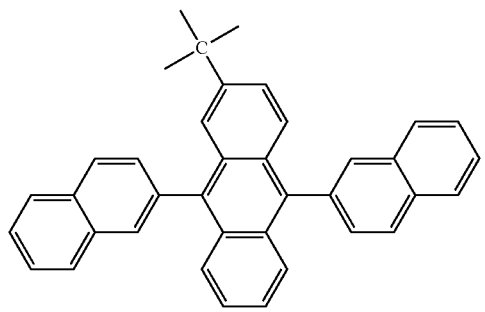

Example 28

An organic EL device was fabricated under the same conditions used in Example 27, except that the compound of Example 2 of the present invention (Compound 10) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 29

An organic EL device was fabricated under the same conditions used in Example 27, except that the compound of Example 3 of the present invention (Compound 42) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 30

An organic EL device was fabricated under the same conditions used in Example 27, except that the compound of Example 4 of the present invention (Compound 45) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 31

An organic EL device was fabricated under the same conditions used in Example 27, except that the compound of Example 5 of the present invention (Compound 52) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 32

An organic EL device was fabricated under the same conditions used in Example 27, except that the compound of Example 6 of the present invention (Compound 55) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 33

An organic EL device was fabricated under the same conditions used in Example 27, except that the compound of Example 7 of the present invention (Compound 59) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 34

An organic EL device was fabricated under the same conditions used in Example 27, except that the compound of Example 8 of the present invention (Compound 61) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 35

An organic EL device was fabricated under the same conditions used in Example 27, except that the compound of Example 9 of the present invention (Compound 87) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 36

An organic EL device was fabricated under the same conditions used in Example 27, except that the compound of Example 10 of the present invention (Compound 89) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 37

An organic EL device was fabricated under the same conditions used in Example 27, except that the compound of Example 21 of the present invention (Compound 86) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Example 38

An organic EL device was fabricated under the same conditions used in Example 27, except that the compound of Example 22 of the present invention (Compound 88) was used as the material of the hole blocking layer-electron transport layer 6 and 7 and formed in a thickness of 30 nm, instead of the compound of Example 1 of the present invention (Compound 9). The characteristics of the organic EL device thus fabricated were measured in an atmosphere at ordinary temperature. Table 1 summarizes the results of the emission characteristics measurements performed by applying a DC voltage to the organic EL device thus fabricated.

Comparative Example 1

For comparison, an organic EL device was fabricated under the same conditions used in Example 27, except that $Alq_3$ was used as the material of the electron transport layer 7, instead of forming the hole blocking layer-electron transport layer 6 and 7. The characteristics of the organic EL device thus fabricated were measured in an atmosphere at ordinary temperature. Table 1 summarizes the results of the emission characteristics measurements performed by applying a DC voltage to the organic EL device thus fabricated.

TABLE 1

| | Compound | Voltage [V] (@ 10 mA/cm$^2$) | Luminance [cd/m$^2$] (@ 10 mA/cm$^2$) | Luminous current efficiency [cd/A] (@ 10 mA/cm$^2$) | Power efficiency [lm/W] (@ 10 mA/cm$^2$) |
|---|---|---|---|---|---|
| Example 27 | Compound 9 | 4.95 | 1038 | 10.38 | 6.57 |
| Example 28 | Compound 10 | 4.35 | 1131 | 11.31 | 8.18 |

TABLE 1-continued

|  | Compound | Voltage [V] (@ 10 mA/cm²) | Luminance [cd/m²] (@ 10 mA/cm²) | Luminous current efficiency [cd/A] (@ 10 mA/cm²) | Power efficiency [lm/W] (@ 10 mA/cm²) |
| --- | --- | --- | --- | --- | --- |
| Example 29 | Compound 42 | 4.66 | 925 | 9.25 | 6.24 |
| Example 30 | Compound 45 | 4.55 | 1190 | 11.90 | 8.23 |
| Example 31 | Compound 52 | 5.55 | 960 | 9.60 | 5.45 |
| Example 32 | Compound 55 | 5.21 | 1058 | 10.58 | 6.38 |
| Example 33 | Compound 59 | 4.50 | 980 | 9.80 | 6.83 |
| Example 34 | Compound 61 | 4.81 | 1290 | 12.90 | 8.40 |
| Example 35 | Compound 87 | 5.05 | 1485 | 14.85 | 9.24 |
| Example 36 | Compound 89 | 3.90 | 1180 | 11.80 | 9.50 |
| Example 37 | Compound 86 | 4.28 | 960 | 9.60 | 7.04 |
| Example 38 | Compound 88 | 3.78 | 1093 | 10.93 | 9.09 |
| Comparative Example 1 | Alq$_3$ | 5.80 | 820 | 8.25 | 4.40 |

As can be seen in Table 1, the driving voltage at a current density of 10 mA/cm² was as low as 3.78 to 5.55 V in Examples 27 to 38, compared to 5.80 V for Alq$_3$. There were also improvements in the luminance, luminous current efficiency, and power efficiency measured at a current density of 10 mA/cm².

The measurement results of turn on voltage are as follows.

| Organic EL device | Compound | Turn on voltage [V] |
| --- | --- | --- |
| Example 27 | Compound 9 | 3.0 |
| Example 28 | Compound 10 | 2.9 |
| Example 29 | Compound 42 | 2.9 |
| Example 30 | Compound 45 | 2.8 |
| Example 31 | Compound 52 | 2.9 |
| Example 32 | Compound 55 | 2.9 |
| Example 33 | Compound 59 | 2.8 |
| Example 34 | Compound 61 | 2.9 |
| Example 35 | Compound 87 | 2.9 |
| Example 36 | Compound 89 | 2.8 |
| Example 37 | Compound 86 | 2.8 |
| Example 38 | Compound 88 | 2.8 |
| Comparative Example 1 | Alq$_3$ | 3.2 |

It can be seen that the turn on voltage was lower in Examples 27 to 38 than in Comparative Example 1 that used Alq$_3$.

Example 39

An organic EL device, as illustrated in FIG. 13, was fabricated from a hole transport layer 4, a light emitting layer 5, a hole blocking layer 6, an electron transport layer 7, an electron injection layer 8, and a cathode (aluminum electrode) 9 successively formed by vapor deposition on a glass substrate 1 that had been provided with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole transport layer 4 by forming Compound 122 of the structural formula below over the transparent anode 2 in a thickness of 60 nm at a deposition rate of 6 nm/min. Thereafter, the light emitting layer 5 was formed on the hole transport layer 4 by forming Compounds 123 and 124 of the structural formulae below in a thickness of 30 nm using dual vapor deposition at a deposition rate ratio of compound 123:compound 124=5:95. The hole blocking layer-electron transport layer 6 and 7 were then formed on the light emitting layer 5 by forming the compound of Example 13 of the present invention (Compound 15) in a thickness of 30 nm at a deposition rate of 6 nm/min. Then, the electron injection layer 8 was formed on the hole blocking layer-electron transport layer 6 and 7 by forming lithium fluoride in a thickness of 0.5 nm at a deposition rate of 0.6 nm/min Finally, the cathode 9 was formed by vapor depositing aluminum in a thickness of 150 nm. The characteristics of the organic EL device thus fabricated were measured in an atmosphere at ordinary temperature.

Table 2 summarizes the results of the emission characteristics measurements performed by applying a DC voltage to the organic EL device fabricated with the compound of Example 13 of the present invention (Compound 15).

Example 40

An organic EL device was fabricated under the same conditions used in Example 39, except that the compound of Example 14 of the present invention (Compound 18) was used as the material of the hole blocking layer-electron transport layer 6 and 7 and formed in a thickness of 30 nm, instead of the compound of Example 13 of the present invention (Compound 15). The characteristics of the organic EL device thus fabricated were measured in an atmosphere at ordinary temperature. Table 2 summarizes the results of the emission characteristics measurements performed by applying a DC voltage to the organic EL device thus fabricated.

Example 41

An organic EL device was fabricated under the same conditions used in Example 39, except that the compound of Example 15 of the present invention (Compound 31) was used as the material of the hole blocking layer-electron transport layer 6 and 7 and formed in a thickness of 30 nm, instead of the compound of Example 13 of the present invention (Compound 15). The characteristics of the organic EL device thus fabricated were measured in an atmosphere at ordinary temperature. Table 2 summarizes the results of the emission characteristics measurements performed by applying a DC voltage to the organic EL device thus fabricated.

Example 42

An organic EL device was fabricated under the same conditions used in Example 39, except that the compound of Example 16 of the present invention (Compound 32) was used as the material of the hole blocking layer-electron transport layer 6 and 7 and formed in a thickness of 30 nm, instead of the compound of Example 13 of the present invention (Compound 15). The characteristics of the organic EL device thus fabricated were measured in an atmosphere at ordinary temperature. Table 2 summarizes the results of the emission characteristics measurements performed by applying a DC voltage to the organic EL device thus fabricated.

Example 43

An organic EL device was fabricated under the same conditions used in Example 39, except that the compound of Example 20 of the present invention (Compound 80) was used as the material of the hole blocking layer-electron transport layer 6 and 7 and formed in a thickness of 30 nm, instead of the compound of Example 13 of the present invention (Compound 15). The characteristics of the organic EL device thus fabricated were measured in an atmosphere at ordinary temperature. Table 2 summarizes the results of the emission characteristics measurements performed by applying a DC voltage to the organic EL device thus fabricated.

Example 44

An organic EL device was fabricated under the same conditions used in Example 39, except that the compound of Example 22 of the present invention (Compound 88) was used as the material of the hole blocking layer-electron transport layer 6 and 7 and formed in a thickness of 30 nm, instead of the compound of Example 13 of the present invention (Compound 15). The characteristics of the organic EL device thus fabricated were measured in an atmosphere at ordinary temperature. Table 2 summarizes the results of the emission characteristics measurements performed by applying a DC voltage to the organic EL device thus fabricated.

Comparative Example 2

For comparison, an organic EL device was fabricated under the same conditions used in Example 39, except that $Alq_3$ was used as the material of the electron transport layer 7, instead of forming the hole blocking layer-electron transport layer 6 and 7. The characteristics of the organic EL device thus fabricated were measured in an atmosphere at ordinary temperature. Table 2 summarizes the results of the emission characteristics measurements performed by applying a DC voltage to the organic EL device thus fabricated.

As can be seen in Table 2, the driving voltage at a current density of 10 $mA/cm^2$ was as low as 3.74 to 5.22 V in Examples 39 to 44, compared to 5.26 V for $Alq_3$. There were also improvements in the luminance, luminous current efficiency, and power efficiency measured at a current density of 10 $mA/cm^2$.

The measurement results of turn on voltage are as follows.

| Organic EL device | Compound | Turn on voltage [V] |
|---|---|---|
| Example 39 | Compound 9 | 2.9 |
| Example 40 | Compound 10 | 3.0 |
| Example 41 | Compound 42 | 2.8 |
| Example 42 | Compound 45 | 2.9 |
| Example 43 | Compound 52 | 2.8 |
| Example 44 | Compound 55 | 2.7 |
| Comparative Example 2 | $Alq_3$ | 3.1 |

It can be seen that the turn on voltage was lower in Examples 39 to 44 than in Comparative Example 2 that used $Alq_3$.

It was therefore found that the organic EL device of the present invention had superior luminous efficiency compared with the devices that used the common electron transport material $Alq_3$, and could greatly lower the actual driving voltage.

INDUSTRIAL APPLICABILITY

The compound having a substituted anthracene ring structure and a pyridoindole ring structure of the present invention has good electron injection characteristics, excels in hole blocking ability and heat resistance, and thus has a stable thin-film state. The compound is therefore excellent as a compound for organic EL devices. The organic EL device fabricated with the compound can have high efficiency, a low driving voltage, and thus improved durability. There are potential applications for, for example, home electronic appliances and illuminations.

DESCRIPTION OF REFERENCE NUMERALS AND SIGNS

1 Glass substrate
2 Transparent anode
3 Hole injection layer
4 Hole transport layer
5 Light emitting layer
6 Hole blocking layer
7 Electron transport layer
8 Electron injection layer
9 Cathode

TABLE 2

| | Compound | Voltage [V] (@ 10 $mA/cm^2$) | Luminance [$cd/m^2$] (@ 10 $mA/cm^2$) | Luminous current efficiency [cd/A] (@ 10 $mA/cm^2$) | Power efficiency [lm/W] (@ 10 $mA/cm^2$) |
|---|---|---|---|---|---|
| Example 39 | Compound 15 | 4.95 | 1038 | 10.38 | 6.57 |
| Example 40 | Compound 18 | 4.35 | 1131 | 11.31 | 8.18 |
| Example 41 | Compound 31 | 4.66 | 925 | 9.25 | 6.24 |
| Example 42 | Compound 32 | 4.55 | 1190 | 11.90 | 8.23 |
| Example 43 | Compound 80 | 5.55 | 960 | 9.60 | 5.45 |
| Example 44 | Compound 88 | 5.21 | 1058 | 10.58 | 6.38 |
| Comparative Example 1 | $Alq_3$ | 5.80 | 820 | 8.25 | 4.40 |

The invention claimed is:

1. A compound of the following general formula (1) having a substituted anthracene ring structure and a pyridoindole ring structure

[Chemical Formula 1]

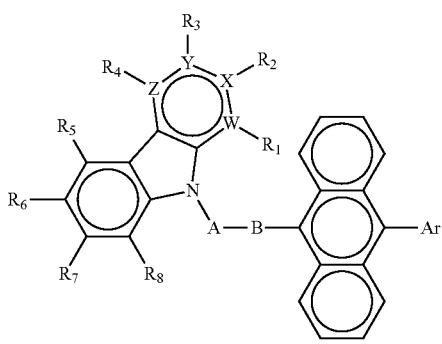

(1)

wherein, Ar represents substituted or unsubstituted aromatic hydrocarbon, or substituted or unsubstituted condensed polycyclic aromatic, A represents a divalent group of substituted or unsubstituted aromatic hydrocarbon, a divalent group of a substituted or unsubstituted aromatic heterocyclic ring, or a divalent group of substituted or unsubstituted condensed polycyclic aromatic, B represents a single bond, a divalent group of substituted or unsubstituted aromatic hydrocarbon, a divalent group of a substituted or unsubstituted aromatic heterocyclic ring, or a divalent group of substituted or unsubstituted condensed polycyclic aromatic, $R_1$ to $R_8$ may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, and Z represent a carbon atom; Y represents a nitrogen atom; and the nitrogen atom does not have the substituents R3; with the proviso that when A and B are aromatic heterocyclic groups, A and B cannot simultaneously be represented by pyridyl groups.

2. A compound of the following general formula (1) having a substituted anthracene ring structure and a pyridoindole ring structure

[Chemical Formula 1]

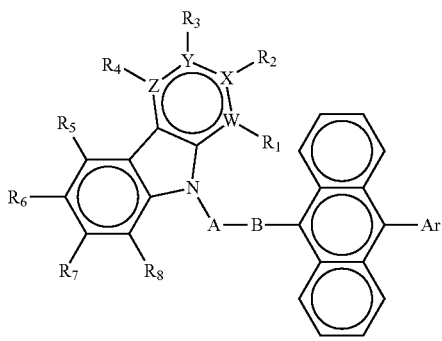

(1)

wherein, Ar represents substituted or unsubstituted aromatic hydrocarbon, or substituted or unsubstituted condensed polycyclic aromatic, A represents a divalent group of substituted or unsubstituted aromatic hydrocarbon, B represents a divalent group of substituted or unsubstituted aromatic hydrocarbon, or a divalent group of substituted or unsubstituted condensed polycyclic aromatic, $R_1$ to $R_8$ may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituents $R_1$ to $R_4$.

3. A compound of the following general formula (1) having a substituted anthracene ring structure and a pyridoindole ring structure

[Chemical Formula 1]

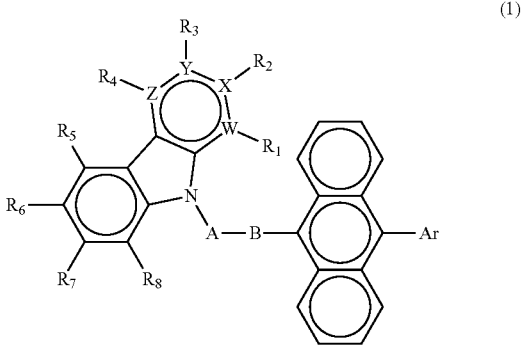

(1)

wherein, Ar represents substituted or unsubstituted aromatic hydrocarbon, or substituted or unsubstituted condensed polycyclic aromatic, A represents a divalent group of a substituted or unsubstituted aromatic heterocyclic ring, B represents a single bond or a divalent group of a substituted or unsubstituted aromatic heterocyclic ring, $R_1$ to $R_8$ may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituents $R_1$ to $R_4$; with the proviso that when A and B are aromatic heterocyclic groups, A and B cannot simultaneously be represented by pyridyl groups.

4. A compound of the following general formula (1) having a substituted anthracene ring structure and a pyridoindole ring structure

[Chemical Formula 1]

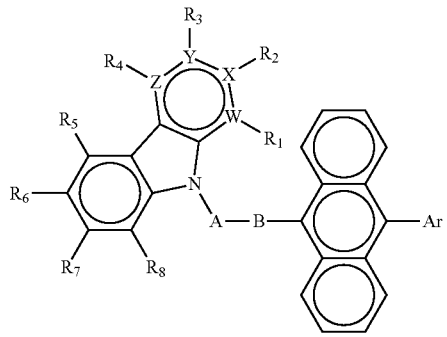

(1)

wherein, Ar represents substituted or unsubstituted aromatic hydrocarbon, or substituted or unsubstituted condensed polycyclic aromatic, A represents a divalent group of substituted or unsubstituted condensed polycyclic aromatic, B represents a divalent group of substituted or unsubstituted aromatic hydrocarbon, or a divalent group of substituted or unsubstituted condensed polycyclic aromatic, $R_1$ to $R_8$ may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituents $R_1$ to $R_4$.

5. A compound of the following general formula (1) having a substituted anthracene ring structure and a pyridoindole ring structure

[Chemical Formula 1]

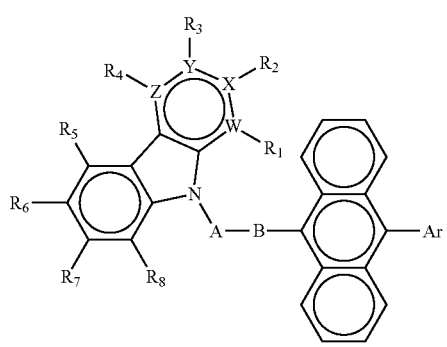

(1)

wherein, Ar represents substituted or unsubstituted aromatic hydrocarbon, or substituted or unsubstituted condensed polycyclic aromatic, A represents one selected from a group consisting of substituted or unsubstituted biphenylylene, terphenylylene, tetrakisphenylene, naphthylene, anthrylene, phenanthrylene, fluorenylene, and phenanthrolylene, B represents a single bond, $R_1$ to $R_8$ may be the same or different, and represent a hydrogen atom, a deuterium atom, a fluorine atom, a chlorine atom, cyano, linear or branched alkyl of 1 to 6 carbon atoms that may have a substituent, substituted or unsubstituted aromatic hydrocarbon, a substituted or unsubstituted aromatic heterocyclic group, or substituted or unsubstituted condensed polycyclic aromatic, and W, X, Y, and Z represent a carbon atom or a nitrogen atom, where only one of W, X, Y, and Z is a nitrogen atom, and, in this case, the nitrogen atom does not have the substituents $R_1$ to $R_4$.

6. An organic electroluminescent device that comprises a pair of electrodes, and one or more organic layers sandwiched between the pair of electrodes, wherein the compound of claim 1 is used as a constituent material of at least one of the organic layers.

7. The organic electroluminescent device according to claim 6, wherein the organic layer is an electron transport layer, and the compound of the general formula (1) is used as at least one of the constituent materials in the electron transport layer.

8. The organic electroluminescent device according to claim 6, wherein the organic layer is a hole blocking layer, and the compound of the general formula (1) is used as at least one of the constituent materials in the hole blocking layer.

9. The organic electroluminescent device according to claim 6, wherein the organic layer is a light emitting layer, and the compound of the general formula (1) is used as at least one of the constituent materials in the light emitting layer.

10. The organic electroluminescent device according to claim 6, wherein the organic layer is an electron injection layer, and the compound of the general formula (1) is used as at least one of the constituent materials in the electron injection layer.

11. An organic electroluminescent device that comprises a pair of electrodes, and one or more organic layers sandwiched between the pair of electrodes, wherein the compound of claim 3 is used as a constituent material of at least one of the organic layers.

12. An organic electroluminescent device that comprises a pair of electrodes, and one or more organic layers sandwiched between the pair of electrodes, wherein the compound of claim 5 is used as a constituent material of at least one of the organic layers.

\* \* \* \* \*